US006200312B1

(12) United States Patent
Zikorus et al.

(10) Patent No.: US 6,200,312 B1
(45) Date of Patent: *Mar. 13, 2001

(54) EXPANDABLE VEIN LIGATOR CATHETER HAVING MULTIPLE ELECTRODE LEADS

(75) Inventors: Arthur W. Zikorus; Mark P. Parker, both of San Jose; Christopher S. Jones, Sunnyvale; Douglas M. Petty, Pleasonton; Brian E. Farley, Los Altos; Joseph M. Tartaglia, Morgan Hill, all of CA (US)

(73) Assignee: Vnus Medical Technologies, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/927,251

(22) Filed: Sep. 11, 1997

(51) Int. Cl.[7] .................................................. A61B 17/38
(52) U.S. Cl. .............................................. 606/32; 606/41
(58) Field of Search .................................. 606/32, 34, 40, 606/41, 42, 46, 48, 49, 50, 159; 607/96, 98, 100–102, 105, 106, 113, 115, 116

(56) References Cited

U.S. PATENT DOCUMENTS

| 373,399 | 11/1887 | Hamilton . |
| 659,409 | 10/1900 | Mosher . |

(List continued on next page.)

(List continued on next page.)

FOREIGN PATENT DOCUMENTS

| 35 16830 A1 | 11/1986 | (DE) . |
| 0 189 329 A2 | 7/1986 | (EP) . |

| WO 92/12681 | 8/1992 | (WO) . |
| WO 94/07446 | 4/1994 | (WO) . |
| WO 95/10322 | 4/1995 | (WO) . |

OTHER PUBLICATIONS

Don Crockett, Jr., M.D., et al., Preliminary Experience with an Endovascular Catheter for Electrocagulation of Peripheral Veins, The Journal of Vascular Technology, Winter 1996, at 19–22.

(List continued on next page.)

Primary Examiner—Linda C. M. Dvorak
Assistant Examiner—Rosiland Kearney
(74) Attorney, Agent, or Firm—Fulwider Patton Lee & Utecht, LLP

(57) ABSTRACT

A catheter includes a plurality of primary leads to deliver energy for ligating a hollow anatomical structure. Each of the primary leads includes an electrode located at the working end of the catheter. Separation is maintained between the primary leads such that each primary lead can individually receive power of selected polarity. The primary leads are constructed to expand outwardly to place the electrodes into apposition with an anatomical structure. High frequency energy can be applied from the leads to create a heating effect in the surrounding tissue of the anatomical structure. The diameter of the hollow anatomical structure is reduced by the heating effect, and the electrodes of the primary leads are moved closer to one another. Where the hollow anatomical structure is a vein, energy is applied until the diameter of the vein is reduced to the point where the vein is occluded. In one embodiment, a secondary lead is surrounded by the primary leads, and extends beyond the primary leads. The secondary lead includes an electrode at the working end of the catheter. The secondary lead can have a polarity opposite to the polarity of the primary leads in a bipolar configuration. The polarity of the leads can be switched and the catheter can be moved during treatment to ligate an extended length of the vein. The catheter can include a lumen to accommodate a guide wire or to allow fluid delivery.

81 Claims, 10 Drawing Sheets

U.S. PATENT DOCUMENTS

| | | |
|---|---|---|
| 833,759 | 10/1906 | Sourwine . |
| 985,865 | 3/1911 | Turner, Jr. . |
| 3,230,957 | 1/1966 | Seifert . |
| 3,301,258 | 1/1967 | Werner et al. . |
| 3,557,794 | 1/1971 | Van Patten . |
| 3,920,021 | 11/1975 | Hiltebrandt . |
| 4,016,886 | 4/1977 | Doss et al. . |
| 4,043,338 | 8/1977 | Homm et al. . |
| 4,119,102 | 10/1978 | LeVeen . |
| 4,154,246 | 5/1979 | LeVeen . |
| 4,312,364 | 1/1982 | Convert et al. . |
| 4,346,715 | 8/1982 | Gammell . |
| 4,522,205 | 6/1985 | Taylor et al. . |
| 4,643,186 | 2/1987 | Rosen et al. . |
| 4,660,571 | 4/1987 | Hess et al. . |
| 4,664,120 | 5/1987 | Hess . |
| 4,699,147 | 10/1987 | Chilson et al. . |
| 4,709,698 | 12/1987 | Johnston et al. . |
| 4,765,331 | 8/1988 | Petruzzi et al. . |
| 4,776,349 | 10/1988 | Nashef et al. . |
| 4,807,620 | 2/1989 | Strul et al. . |
| 4,823,812 | 4/1989 | Eshel et al. . |
| 4,945,912 | 8/1990 | Langberg . |
| 4,966,597 | 10/1990 | Cosman . |
| 4,976,711 | 12/1990 | Parins et al. . |
| 4,979,948 | 12/1990 | Geddes et al. . |
| 5,010,894 | 4/1991 | Edhag . |
| 5,057,107 | 10/1991 | Parins et al. . |
| 5,078,717 | 1/1992 | Parins et al. . |
| 5,117,828 | 6/1992 | Metzger et al. . |
| 5,122,137 | 6/1992 | Lennox . |
| 5,156,151 | 10/1992 | Imran . |
| 5,188,602 | 2/1993 | Nichols . |
| 5,215,103 | 6/1993 | Desai . |
| 5,255,678 | 10/1993 | Deslauriers et al. . |
| 5,263,493 | 11/1993 | Avitall . |
| 5,275,610 | 1/1994 | Eberbach . |
| 5,293,869 | 3/1994 | Edwards et al. . |
| 5,383,917 | 1/1995 | Desai et al. . |
| 5,397,339 | 3/1995 | Desai . |
| 5,405,322 | 4/1995 | Lennox et al. . |
| 5,409,000 | 4/1995 | Imran . |
| 5,411,025 | 5/1995 | Webester, Jr. . |
| 5,423,815 | 6/1995 | Fugo . |
| 5,437,664 | 8/1995 | Cohen et al. . |
| 5,449,381 | 9/1995 | Imran . |
| 5,458,596 | 10/1995 | Lax et al. . |
| 5,465,717 | 11/1995 | Imran et al. . |
| 5,505,730 | 4/1996 | Edwards . |
| 5,514,130 | 5/1996 | Baker . |
| 5,545,161 | 8/1996 | Imran . |
| 5,556,396 | 9/1996 | Cohen et al. . |
| 5,810,804 * | 9/1998 | Gough et al. ............................ 606/41 |
| 5,817,092 * | 10/1998 | Behl ......................................... 606/41 |
| 5,868,740 | 2/1999 | LeVeen et al. .......................... 606/41 |
| 5,916,235 | 6/1999 | Guglielmi . |

OTHER PUBLICATIONS

Samuel R. Money, M.D., Endovascular Elecrtroablation of Peripheral Veins, 22 Annual Symposium, Current Critical Problems, New Horizons and Techniques in Vascular and Endovascular Surgery (Nov. 1995).

Kevin O'Reilly, Endovenous Diathermy Sclerosis AE a Unit of the Armamentarium for the Attack on Varicose Veins, The Medical Journal of Australia, Jun. 1, 1974, at 900.

Francis Brunelle, M.D., et al., A Bipolar Electrode for Vascular Electrocoagulation with Alternating Current, Technical Notes, Oct. 1980, at 239–240.

Yutaka Ogawa, M.D., et al., Electrothrombosis As a Treatment of Cirsoid Angioma in the Face and Scalp and Varicosis of the Leg, Plastic and Reconstructive Surgery, Sep. 1982, vol. 3, at 310–318.

Harold Aaron, M.D., et al., The Medical Letter on Drugs and Therapeutics, Jul. 12, 1968, at 53–55.

* cited by examiner

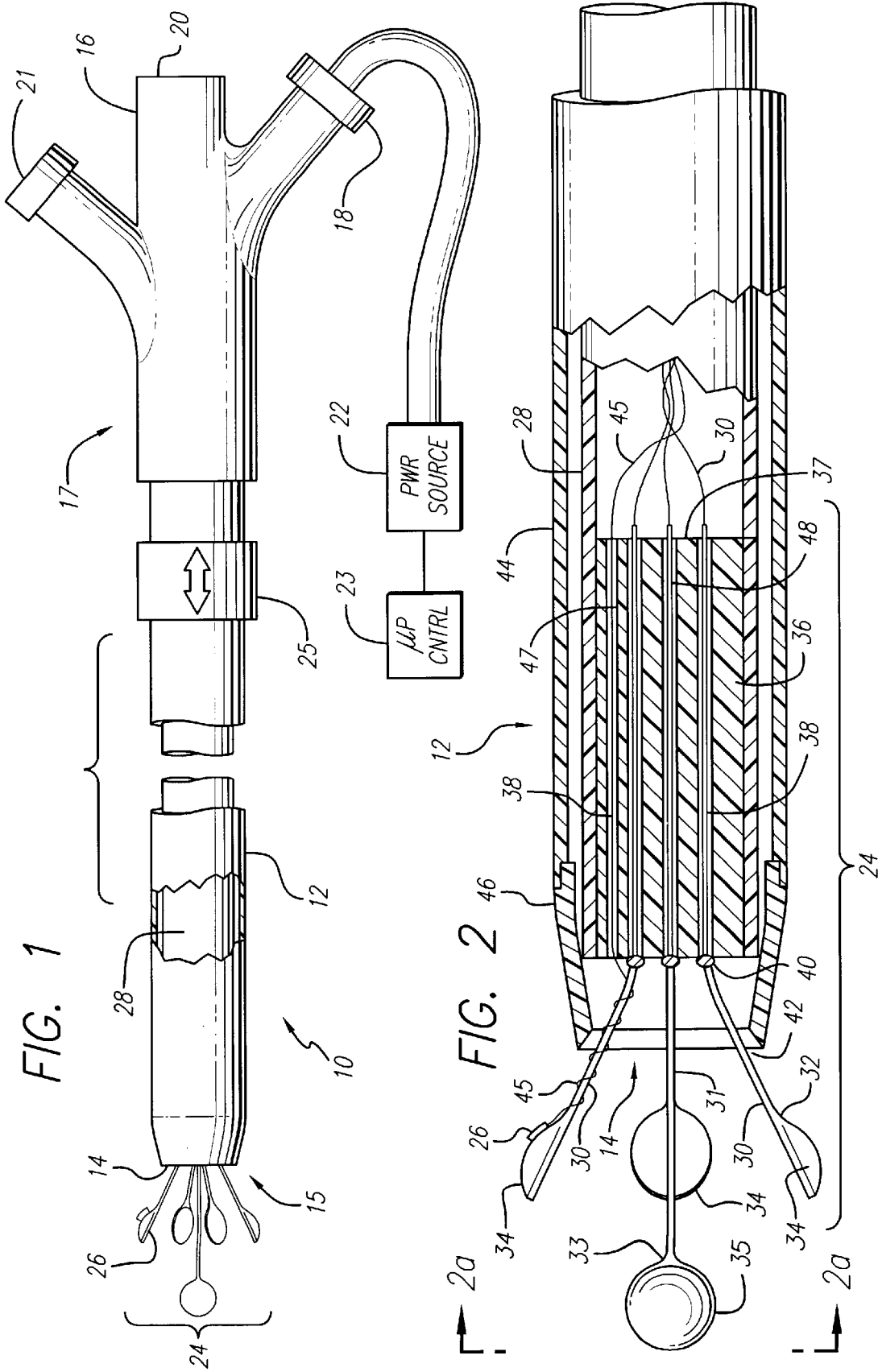

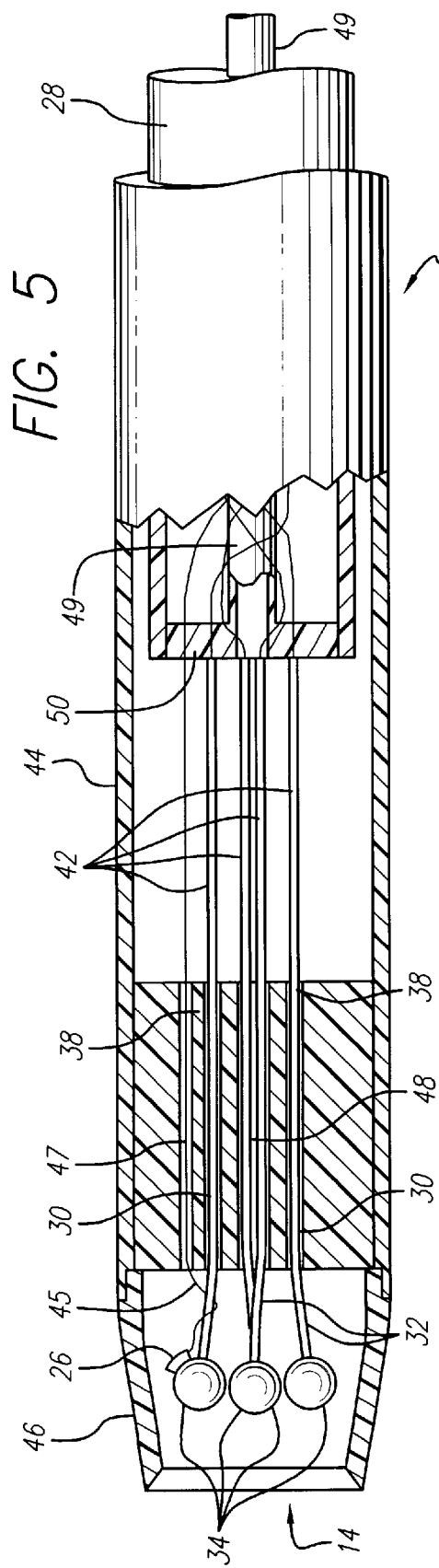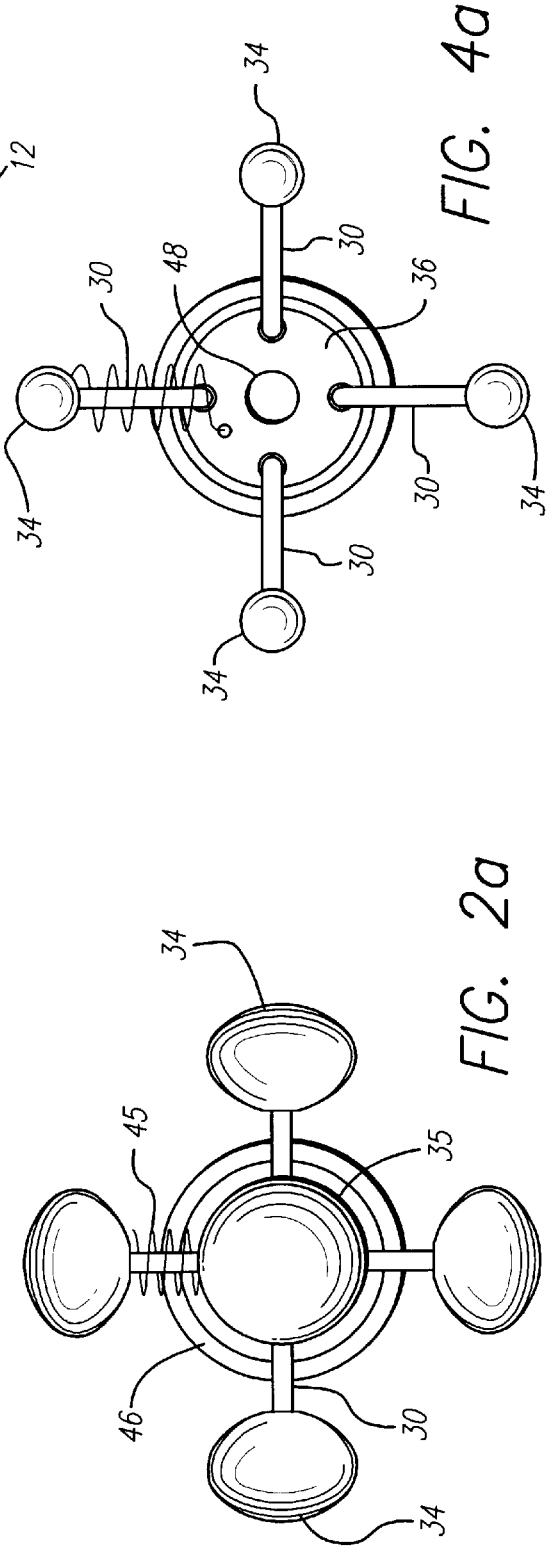

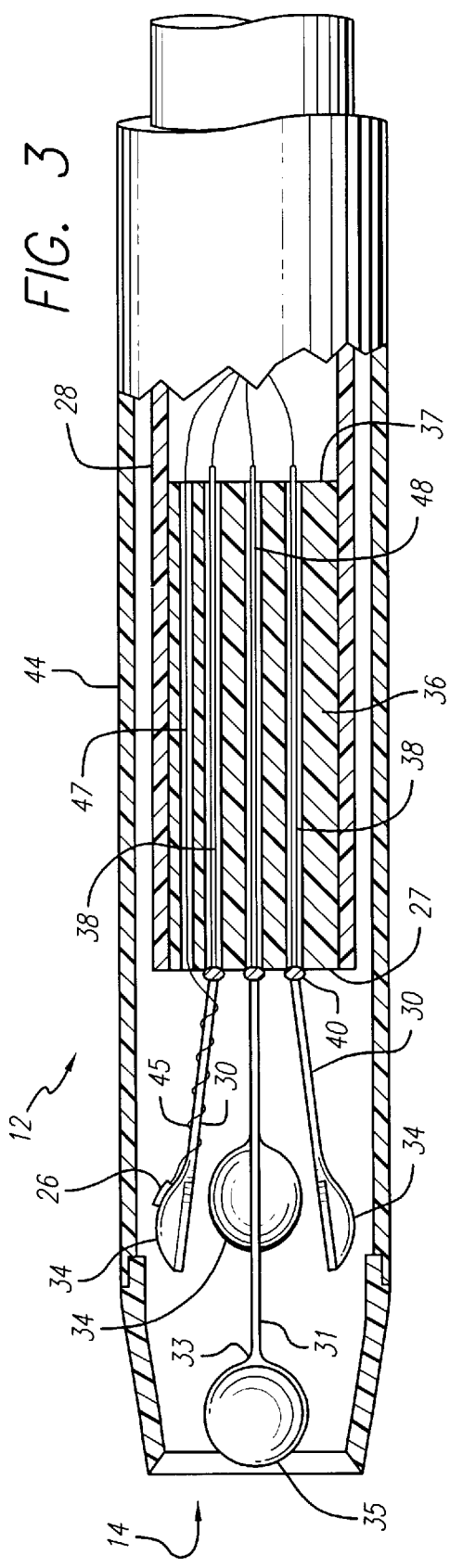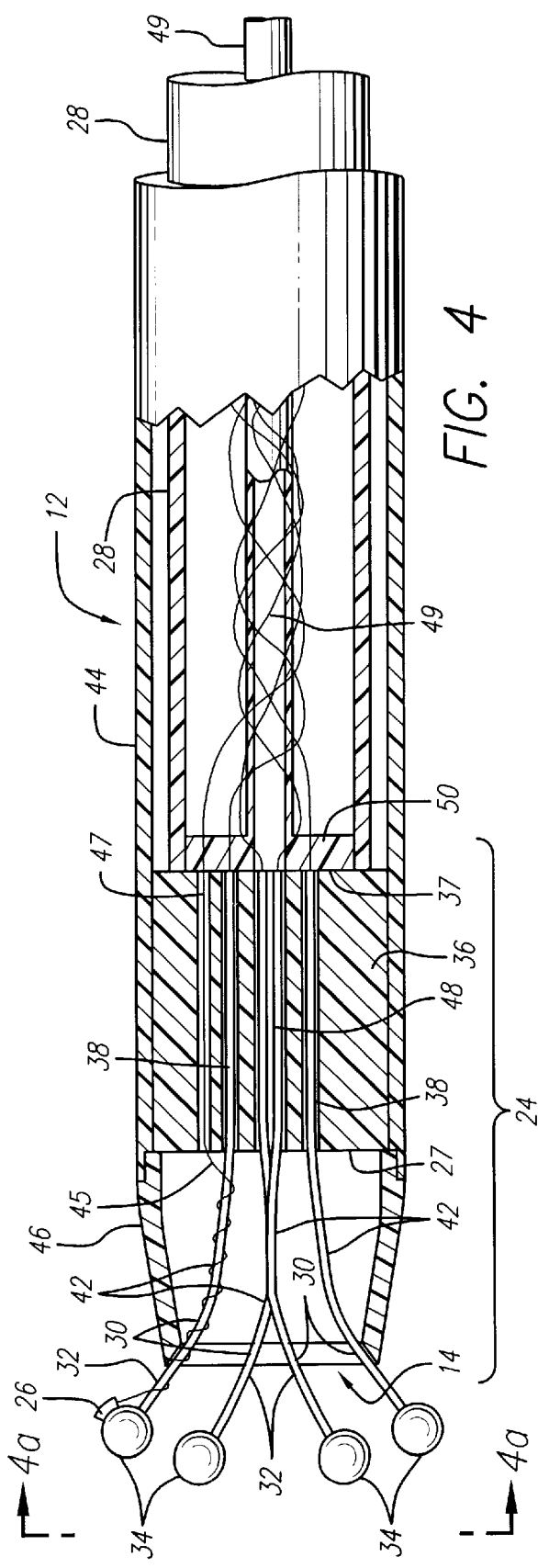

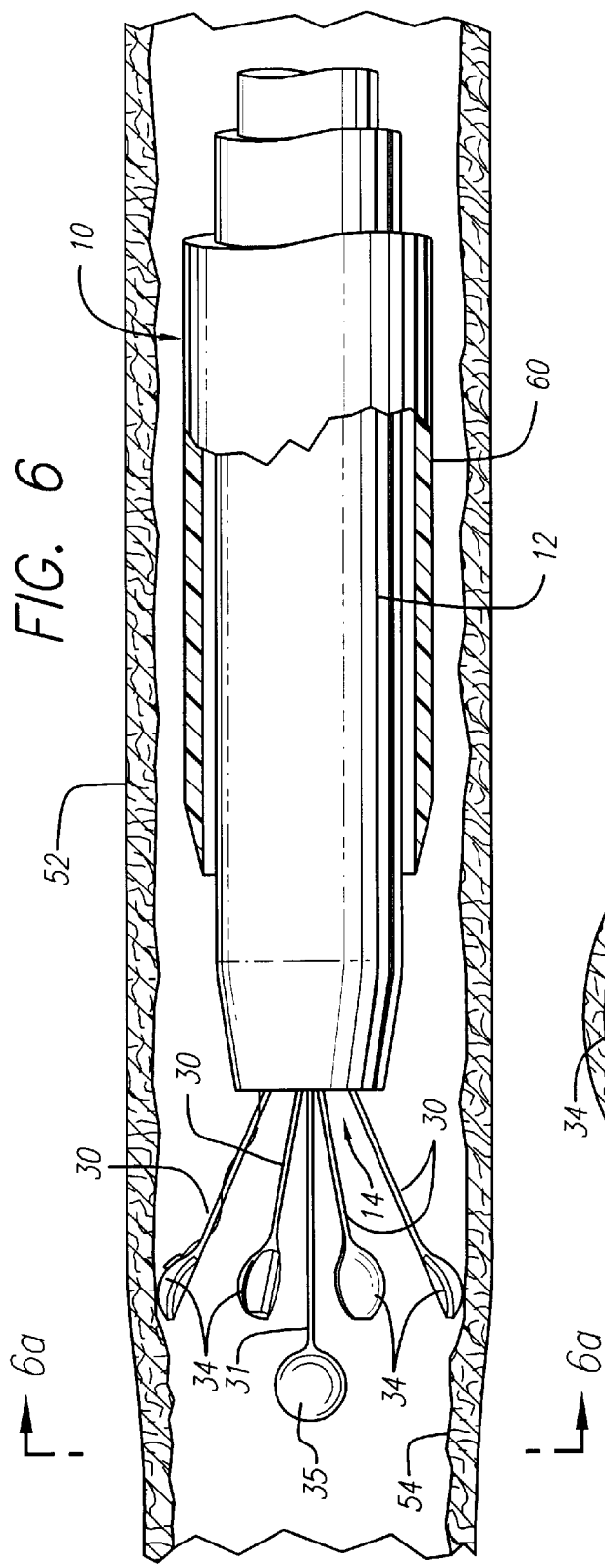

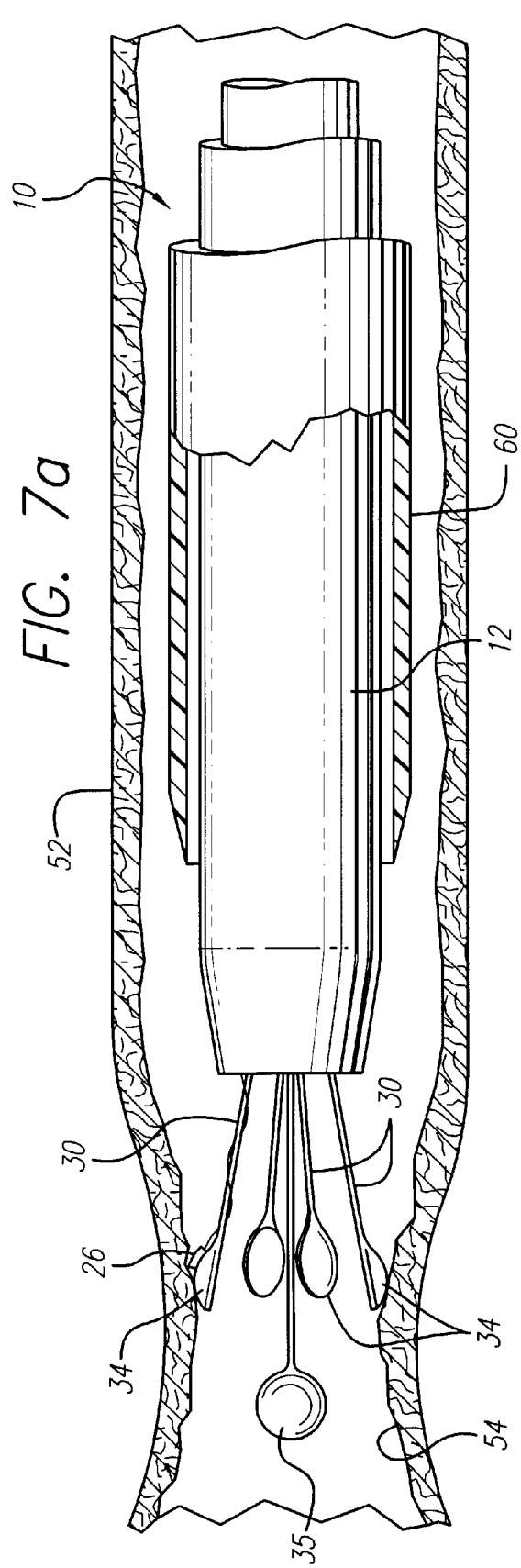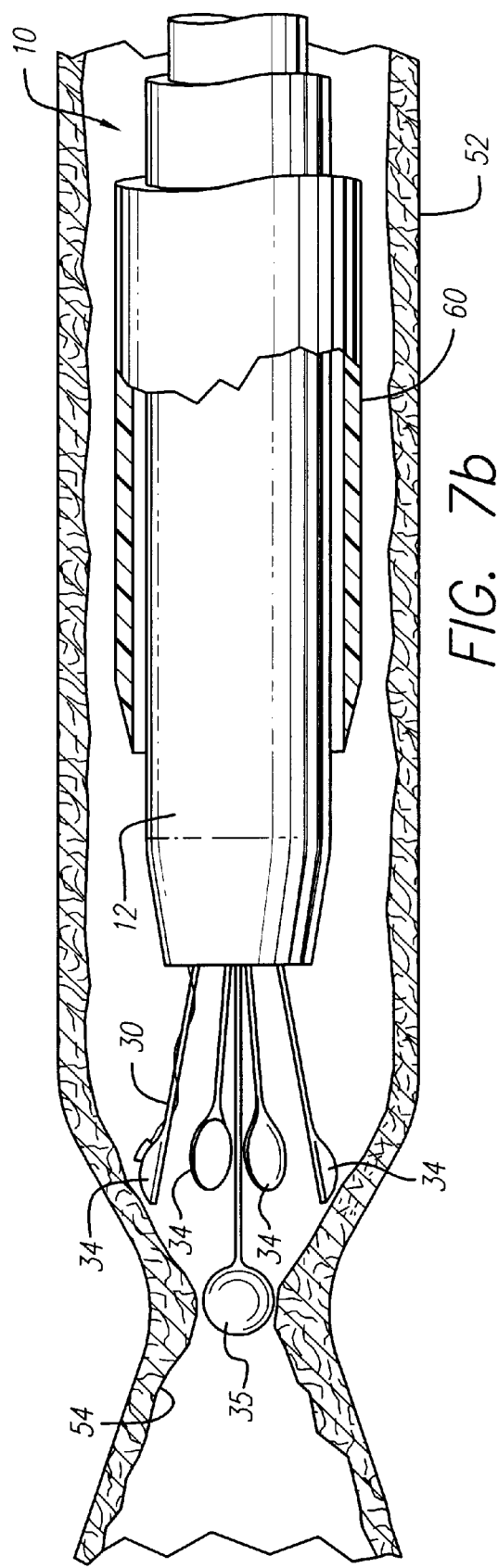

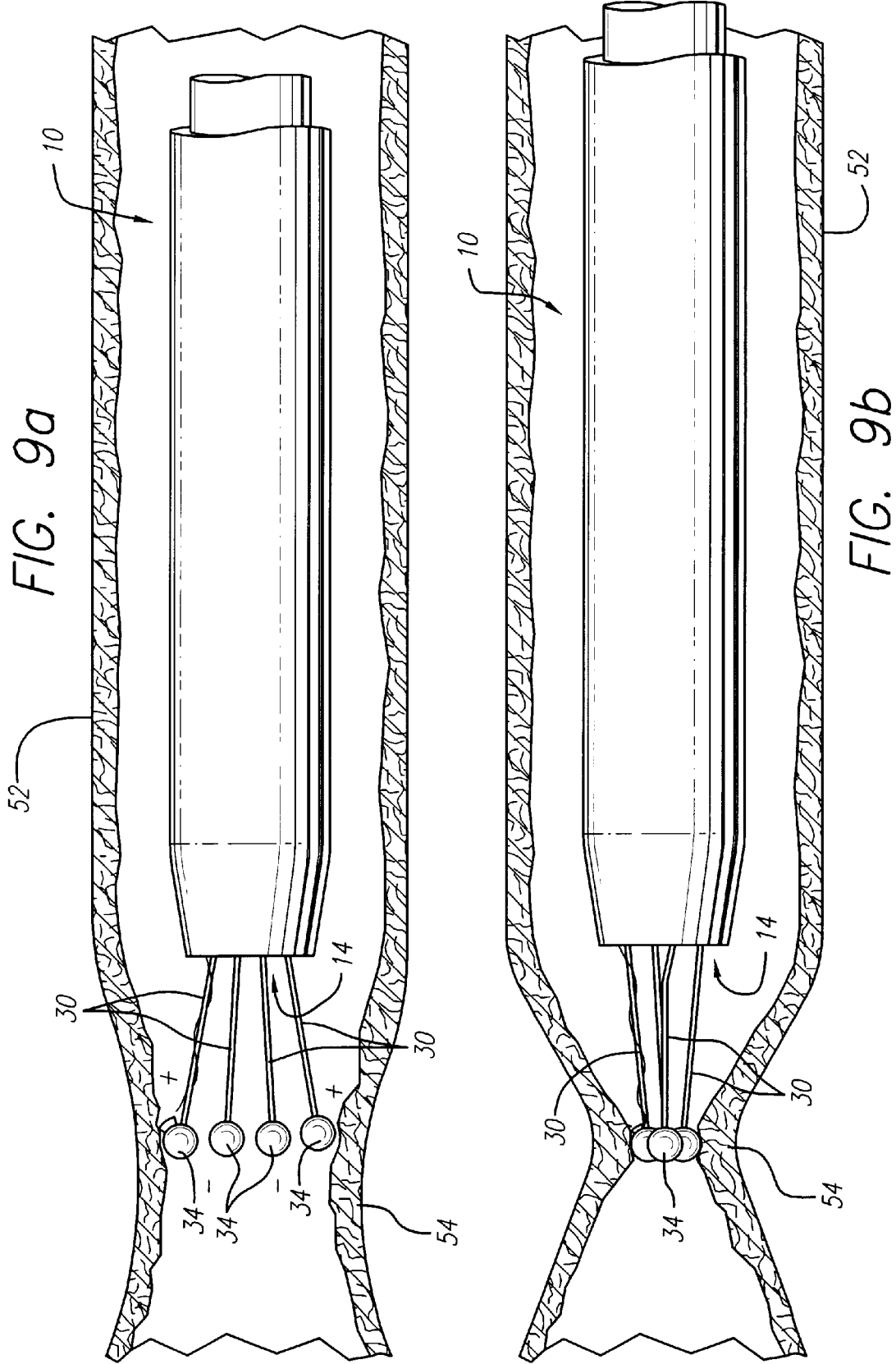

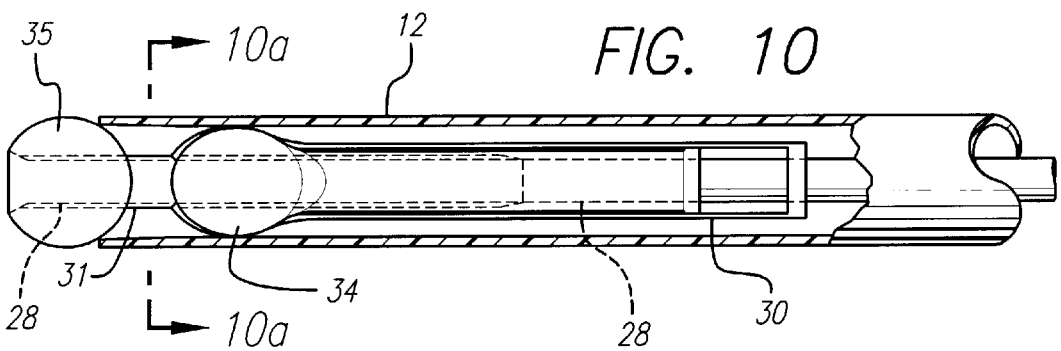
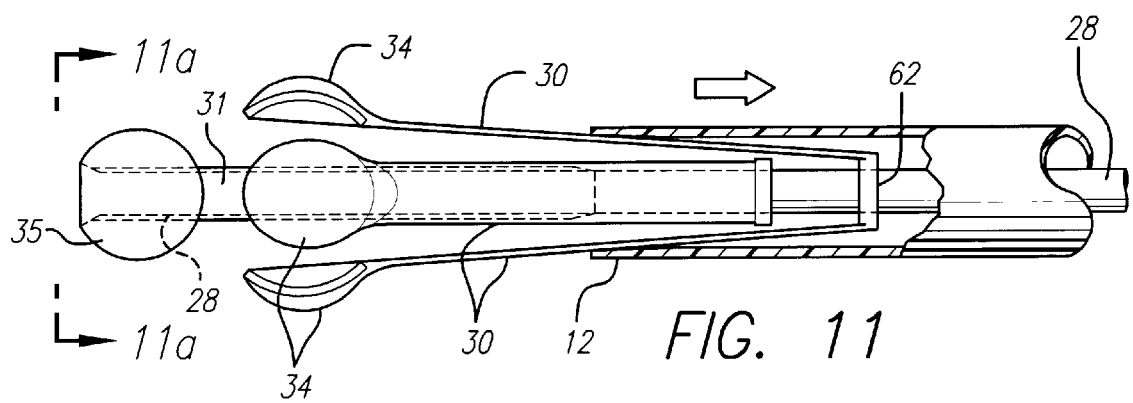
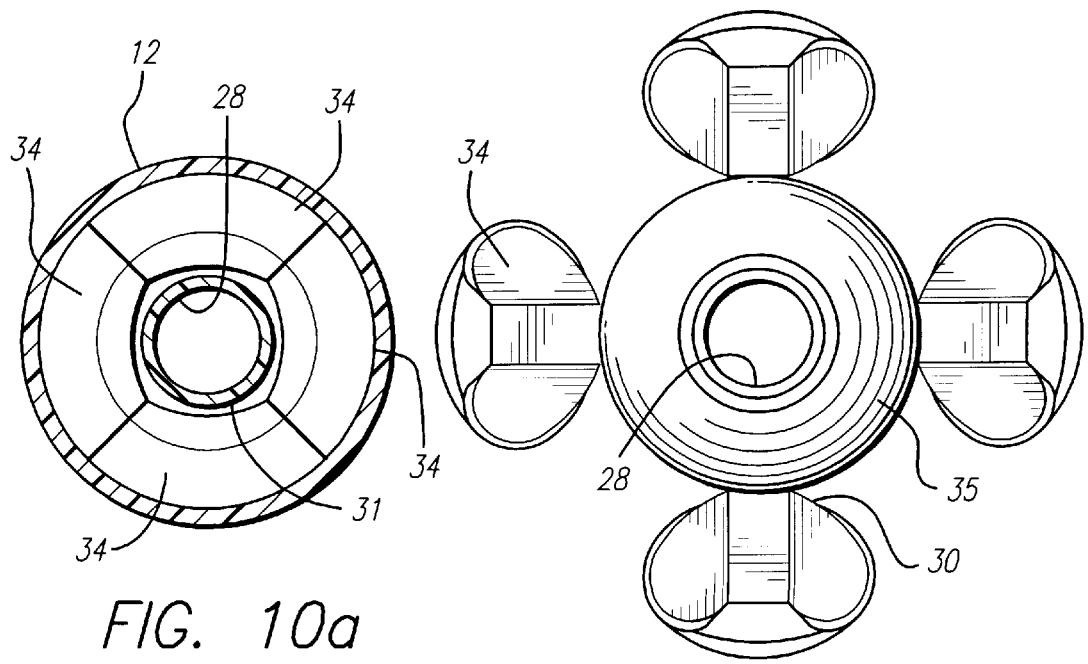

EXPANDABLE VEIN LIGATOR CATHETER HAVING MULTIPLE ELECTRODE LEADS

BACKGROUND OF THE INVENTION

The invention relates generally to a method and apparatus for applying energy to shrink a hollow anatomical structure such as a vein, and more particularly, to a method and apparatus using an electrode device having multiple leads for applying said energy.

The human venous system of the lower limbs consists essentially of the superficial venous system and the deep venous system with perforating veins connecting the two systems. The superficial system includes the long or great saphenous vein and the short saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood which, under retrograde blood pressure, forces the free surfaces of the cusps together to prevent retrograde flow of the blood and allows only antegrade blood flow to the heart. When an incompetent valve is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional valvular failure. Two venous conditions which often result from valve failure are varicose veins and more symptomatic chronic venous insufficiency.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments of vein insufficiency include surgical procedures such as vein stripping, ligation, and occasionally, vein-segment transplant.

Ligation involves the cauterization or coagulation of vascular lumina using electrical energy applied through an electrode device. An electrode device is introduced into the vein lumen and positioned so that it contacts the vein wall. Once properly positioned, RF energy is applied to the electrode device thereby causing the vein wall to shrink in cross-sectional diameter. A reduction in cross-sectional diameter, as for example from 5 mm (0.2 in) to 1 mm (0.04 in), significantly reduces the flow of blood through the vein and results in an effective ligation. Though not required for effective ligation, the vein wall may completely collapse thereby resulting in a full-lumen obstruction that blocks the flow of blood through the vein.

One apparatus for performing venous ligation includes a tubular shaft having an electrode device attached at the distal tip. Running through the shaft, from the distal end to the proximal end, are electrical leads. At the proximal end of the shaft, the leads terminate at an electrical connector, while at the distal end of the shaft the leads are connected to the electrode device. The electrical connector provides the interface between the leads and a power source, typically an RF generator. The RF generator operates under the guidance of a control device, usually a microprocessor.

The ligation apparatus may be operated in either a monopolar and bipolar configuration. In the monopolar configuration, the electrode device consists of an electrode that is either positively or negatively charged. A return path for the current passing through the electrode is provided externally from the body, as for example by placing the patient in physical contact with a large low-impedance pad. The current flows from the ligation device to the low impedance pad. In a bipolar configuration, the electrode device consists of a pair of oppositely charged electrodes separated by a dielectric material. Accordingly, in the bipolar mode, the return path for current is provided by the electrode device itself. The current flows from one electrode, through the tissue, and returns by way of the oppositely charged electrode.

To protect against tissue damage; i.e., charring, due to cauterization caused by overheating, a temperature sensing device is attached to the electrode device. The temperature sensing device may be a thermocouple that monitors the temperature of the venous tissue. The thermocouple interfaces with the RF generator and the controller through the shaft and provides electrical signals to the controller which monitors the temperature and adjusts the energy applied to the tissue, through the electrode device, accordingly.

The overall effectiveness of a ligation apparatus is largely dependent on the electrode device contained within the apparatus. Monopolar and bipolar electrode devices that comprise solid devices having a fixed shape and size limit the effectiveness of the ligating apparatus for several reasons. Firstly, a fixed-size electrode device typically contacts the vein wall at only one point on the circumference or inner diameter of the vein wall. As a result, the application of RF energy is highly concentrated within the contacting venous tissue, while the flow of RF current through the remainder of the venous tissue is disproportionately weak. Accordingly, the regions of the vein wall near the point of contact collapse at a faster rate then other regions of the vein wall, resulting in non-uniform shrinkage of the vein lumen. Furthermore, the overall strength of the occlusion may be inadequate and the lumen may eventually reopen. To avoid an inadequate occlusion RF energy must be applied for an extended period of time. Application of RF energy as such increases the temperature of the blood and usually results in a significant amount of heat-induced coagulum forming on the electrode and in the vein which is not desirable.

Secondly, the effectiveness of a ligating apparatus having a fixed electrode device is limited to certain sized veins. An attempt to ligate a vein having a diameter that is substantially greater than the electrode device can result in not only non-uniform shrinkage of the vein wall as just described, but also insufficient shrinkage of the vein. The greater the diameter of the vein relative to the diameter of the electrode device, the weaker the energy applied to the vein wall at points distant from the point of contact. Accordingly the vein wall is likely to not completely collapse prior to the venous tissue becoming over cauterized at the point of electrode contact. While coagulation as such may initially occlude the vein, such occlusion may only be temporary in that the coagulated blood may eventually dissolve and the vein partially open. One solution for this inadequacy is an apparatus having interchangeable electrode devices with various diameters. Such a solution, however, is both economically inefficient and tedious to use.

Hence those skilled in the art have recognized a need for an expandable electrode device and a method capable of evenly distributing RF energy along a circumferential band of a vein wall where the vein wall is greater in diameter than the electrode device, and thereby provide more predictable and effective occlusion of veins while minimizing the formation of heat-induced coagulum. The invention fulfills these needs and others.

SUMMARY OF THE INVENTION

Briefly, and in general terms, the present invention provides an apparatus and method for applying energy along a generally circumferential band of a vein wall. The application of energy as such results in a more uniform and predictable shrinkage of the vein wall.

In one aspect of the invention, an apparatus for delivering energy to ligate an anatomical structure comprises a catheter having a sheath, a working end, and an opening formed at the working end of the catheter; an inner member disposed within the sheath such that the inner member and the sheath are capable of being moved relative to one another; a plurality of leads, each lead having a distal end, the plurality of leads being coupled with the inner member such that the distal ends of the plurality of leads extend out of the opening at the working end of the catheter when the position of the sheath changes in one direction relative to the inner member, each lead being formed to move the distal end away from a longitudinal axis defined by the sheath when the plurality of leads are extended out the opening; wherein the distal ends of the leads are configured to deliver energy to the anatomical structure.

In another aspect of the invention, the apparatus includes a secondary lead having a secondary distal end. The secondary lead is coupled with the inner member such that the distal end of the secondary lead is extended out of the opening at the working end of the catheter when the position of the inner member changes in one direction relative to the sheath.

In another aspect of the invention, the distal ends of the leads are electrically connected to a power source such that the polarity of each lead can be switched. Where there is a secondary lead electrode, the plurality of leads can be connected to the power source such that the polarity of the leads can be changed independently of the polarity of the secondary lead.

In another aspect, the leads include primary leads which generally surround the secondary lead at the working end of the catheter. The distal ends of the primary leads are located between the distal end of the secondary lead and the inner member.

In yet another aspect, the invention comprises a method of applying energy to a hollow anatomical structure from within the structure. The method includes the step of introducing a catheter into the anatomical structure; the catheter having a working end and a plurality of leads, each lead having a distal end, and each lead being connected to a power source. The method also includes the step of expanding the leads outwardly through the distal orifice and expanding the leads until each electrode contacts the anatomical structure. The method further includes the step of applying energy to the anatomical structure from the distal end of the leads, until the anatomical structure collapses.

In another aspect of the invention, the method also includes the step of introducing a catheter into the anatomical structure where the catheter has a secondary lead that has a distal portion that is greater in length than the primary-lead distal portions and is generally surrounded by the primary leads. The secondary lead also has an electrode at the distal end. The method also includes the steps of extending the primary and secondary leads through the orifice until each primary-lead electrode contacts the anatomical structure, and controlling the power source so that adjacent primary leads are of opposite polarity while maintaining the secondary lead so that it is electrically neutral. Upon collapse of the anatomical structure around the primary leads, the polarity of the primary leads is switched so that they are all of the same polarity. Upon switching the polarity of the primary leads so that they are of the same polarity, controlling the power source so that the secondary lead is of opposite polarity relative to the primary leads. The method, in a further aspect, comprises the step of moving the catheter in the anatomical structure while continuing to apply energy to the anatomical structure to lengthen the area of ligation.

In another aspect of the invention, external compression is used to initially force the wall of the vein to collapse toward the catheter. The application of energy molds the vein to durably assume the collapsed state initially achieved mechanically by the external compression. A tourniquet can be used to externally compress or flatten the anatomical structure and initially reduce the diameter of the hollow anatomical structure. The pressure applied by the tourniquet can exsanguinate blood from the venous treatment site, and pre-shape the vein in preparation to be molded to a ligated state. An ultrasound window formed in the tourniquet can be used to facilitate ultrasound imaging of the anatomical structure being treated through the window.

These and other aspects and advantages of the present invention will become apparent from the following more detailed description, when taken in conjunction with the accompanying drawings which illustrate, by way of example, embodiments of the invention.

BRIEF DESCRIPTION OF THE DRAWINGS

FIG. 1 is a diagram of an energy application system with a partial cutaway view of a catheter showing both the working end and the connecting end and incorporating a preferred embodiment of the present invention;

FIG. 2 is a cross-sectional view of the working end of a first embodiment of a catheter in accordance with the invention depicting the electrodes in a fully extended position;

FIG. 2a is an end view of the working end of the first embodiment of the catheter taken along line 2a—2a of FIG. 2;

FIG. 3 is a cross-sectional view of the working end of the first embodiment depicting the electrodes in a fully retracted position;

FIG. 4 is a cross-sectional view of the working end of a second catheter in accordance with principles of the invention depicting the electrodes in a fully extended position;

FIG. 4a is an end view of the second embodiment of the invention taken along line 4a—4a of FIG. 4;

FIG. 5 is a cross-sectional view of the working end of the second embodiment of the catheter of FIG. 4 depicting the electrodes in a fully retracted position;

FIG. 6 is a cross-sectional view of an anatomical structure containing the catheter of FIG. 2 with the electrodes in apposition with the anatomical structure;

FIG. 6a is an end view of the anatomical structure containing the catheter taken along line 6a—6a of FIG. 6;

FIGS. 7a through 7c are cross-sectional views of the anatomical structure containing a catheter in accordance with the first embodiment of the invention and depicting the anatomical structure at various stages of ligation;

FIGS. 9a and 9b are cross-sectional views of the anatomical structure containing the catheter in accordance with the second embodiment of the invention and depicting the anatomical structure at various stages of ligation;

FIG. 10 is a cross-sectional view of the working end of a third embodiment of a catheter in accordance with the invention depicting the electrodes in a fully extended position;

FIG. 10a is an end view of the working end of the third embodiment of the catheter taken along line 10a—10a of FIG. 10;

FIG. 11 is a cross-sectional view of the working end of the third embodiment depicting the electrodes in a fully retracted position;

FIG. 11a is an end view of the working end of the catheter taken along line 11a —11a of FIG. 11.

DETAILED DESCRIPTION OF THE EMBODIMENTS

Figure 7C:
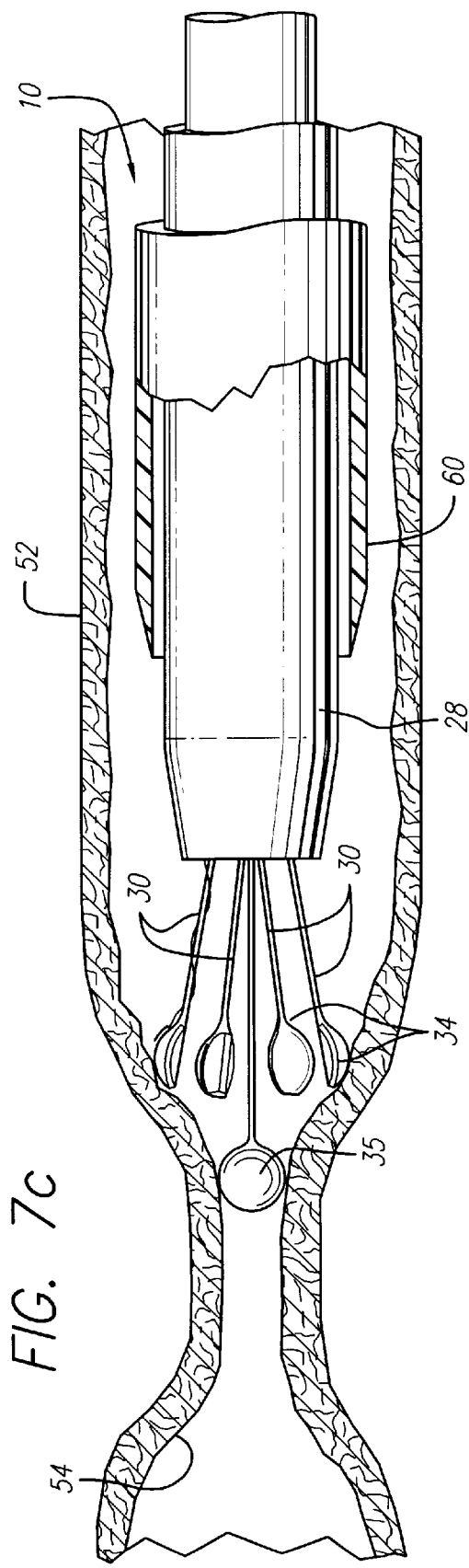
Figure 8:
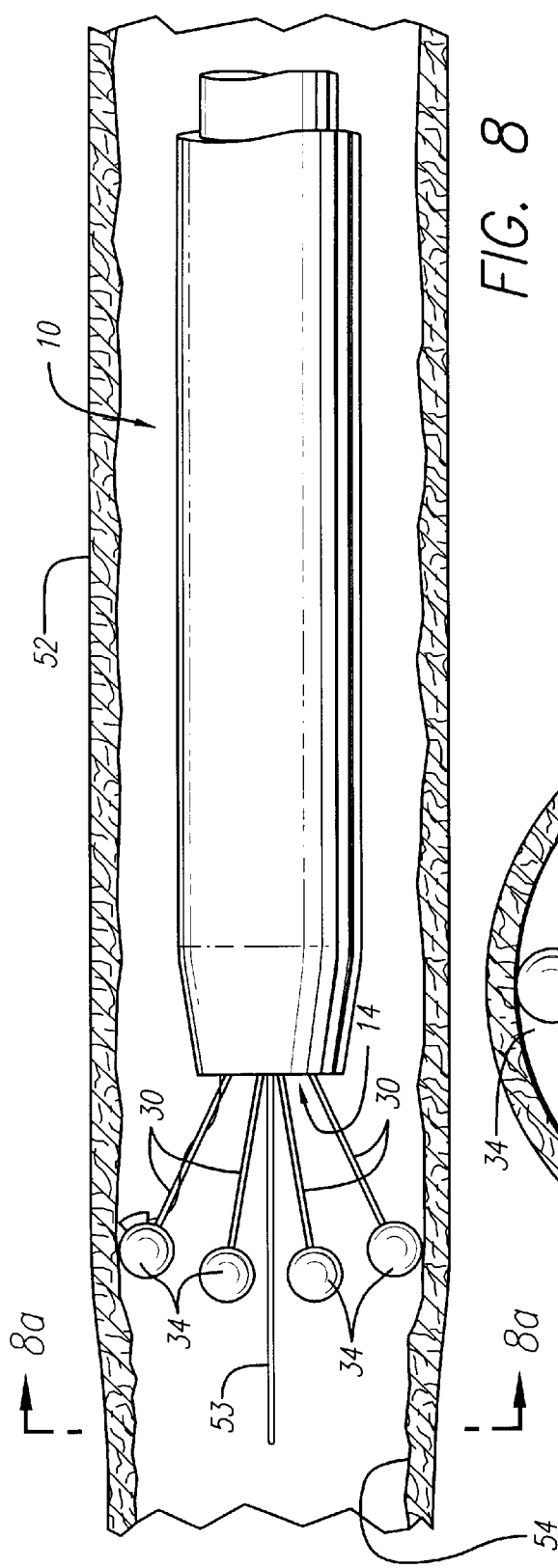
FIG. 8 is a cross-sectional view of an anatomical structure containing a catheter in accordance with the second embodiment of the invention as depicted in FIG. 4.
Figure 8A:
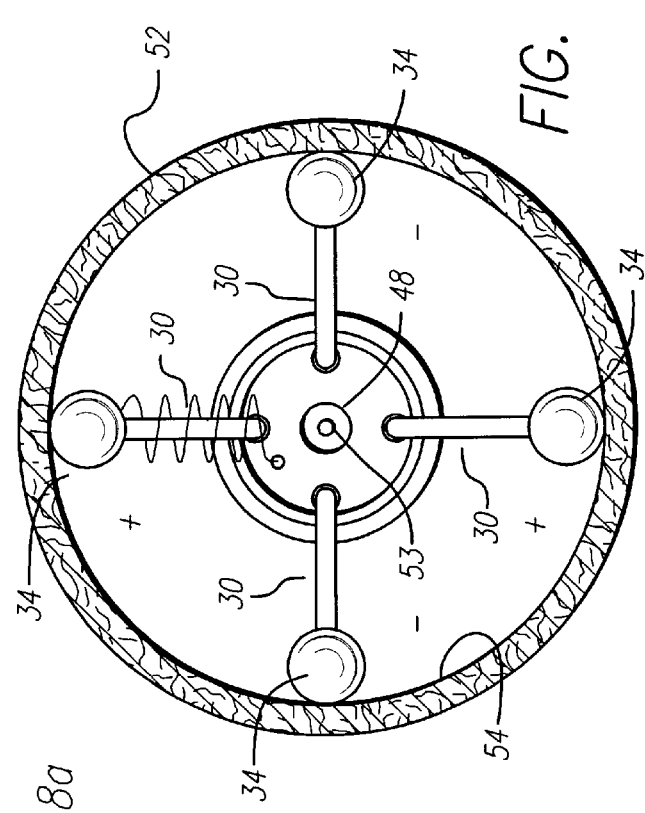
FIG. 8a is an end view of the anatomical structure containing the catheter taken along line 8a—8a of FIG. 8.

Turning now to the drawings with more particularity wherein like reference numerals indicate like or corresponding elements among the figures, shown in FIG. 1 is a catheter 10 for applying energy to an anatomical structure such as a vein. The catheter 10 includes an outer sheath 12 having a distal orifice 14 at its working end 15. The connector end 17 of the outer sheath 12 is attached to a handle 16 that includes an electrical connector 18 for interfacing with a power source 22, typically an RF generator, and a microprocessor controller 23. The power source 22 and microprocessor 23 are usually contained in one unit. The controller 23 controls the power source 22 in response to external commands and data from a sensor, such as a thermocouple, located at an intraluminal venous treatment site. In another embodiment, the user can select a constant power output so that automated temperature control is not present and the user can manually adjust the power output in view of the temperature on a display readout. The catheter 10 includes an expandable electrode device 24 (partially shown) that moves in and out of the outer sheath 12 by way of the distal orifice 14. The electrode device includes a plurality of electrodes which can be expanded by moving the electrodes within the shaft, or by moving the outer shaft relative to the electrodes. Although FIG. 1 illustrates a plurality of electrodes surrounding a single central electrode, different electrode configurations will be described for the catheter.

Contained within the outer sheath 12 is an inner sheath 28 or inner member. A fluid port 21 communicates with the interior of the outer sheath 12. The catheter 10 can be periodically flushed out with saline through the port 21. The flushing fluid can travel between the outer sheath and the inner sheath. The port also allows for the delivery of drug therapies. Flushing out the catheter prevents the buildup of biological fluid, such as blood, within the catheter 10. The treatment area of the hollow anatomical structure such as a vein can be flushed with a fluid such as saline, or a dielectric fluid, in order to evacuate blood from the treatment area of the vein so as to prevent the formation of coagulum or thrombosis. The use of a dielectric fluid can minimize unintended heating effects away from the treatment area. The dielectric fluid prevents the current of RF energy from flowing away from the vein wall.

In one embodiment, the catheter 10 includes a lumen which begins at the distal tip of the outer sheath 12 and runs substantially along the axis of the outer sheath 12 before terminating at the guide-wire port 20 of the handle 16. A guide wire can be introduced through the lumen of the catheter 10 for use in guiding the catheter to the desired treatment site. Where the catheter is sized to treat smaller veins, the outer diameter of the catheter may not allow for a fluid flush between the outer sheath 12 and the inner sheath 28. However, a fluid flush can be introduced through the lumen for the guide wire in such an embodiment.

Referring now to FIGS. 2, 2a, 3, 4, 4a and 5, the outer sheath 12 includes a shell 44 and a tip portion 46. To provide an atraumatic tip for the catheter 10 as it is manipulated through the vein, the tip 46 is preferably tapered inward at its distal end or is "nosecone" shaped. The tip 46, however, can have other shapes that facilitate tracking of the catheter 10 over a guide wire and through the bends in the venous vascular system. The nosecone-shaped tip 46 can, for example, be fabricated from a polymer having a soft durometer, such as 70 Shore A. The shell 44 comprises a biocompatible material having a low coefficient of friction. In one configuration, the outer sheath 12 is sized to fit within a venous lumen and for example may be between 5 and 9 French, which corresponds to a diameter of between 1.7 mm (0.07 in) and 3.0 mm (1.2 in), or other sizes as appropriate.

The electrode device 24 contains a number of leads, including insulated primary leads 30 and, in some embodiments, a secondary lead 31. Preferably, the leads are connected to the power source 22 (FIG. 1) such that the polarity of the leads may be switched as desired. Alternately, a microprocessor controller can be used to switch the polarity, as well as control other characteristics of the power for the electrode device. Thus the electrode device can operate in either a bipolar or a monopolar configuration. When adjacent primary leads 30 have opposite polarity the electrode device 24 operates as a bipolar electrode device. When the primary leads 30 are commonly charged the electrode device 24 can operate as a monopolar electrode device. When the primary leads 30 are commonly charged, and a secondary lead 31 has an opposite polarity, the electrode device 24 operates as a bipolar electrode device. The embodiment of the invention shown in FIGS. 2 and 3 depict an electrode device 24 having four primary leads 30 and a secondary lead 31, while the embodiment of the invention shown in FIGS. 4 and 5 depict an electrode device 24 having only four primary leads. The invention is not limited to four primary leads 30; more or fewer leads may be used in either embodiment. The number of leads can be dependent on the size or diameter of the hollow anatomical structure to be treated. The apposed electrodes should be kept within a certain distance of one another. Larger vessels may require more primary leads to ensure proper current density and proper heat distribution.

The insulation on each of the leads 30, 31 may be removed at the distal end 32, 33 to expose the conductive wire. In the first configuration as shown in FIGS. 2, 2a, and 3, the electrode 34 has a hemispherical shape. In a second configuration, the electrode can have either a generally spherical shape or a spoon shape. As shown in FIGS. 4, 4a and 5, the electrodes have a spoon shape which can be combined to form a sphere or other shape so as to minimize its profile when the vein collapses. The electrodes 34 are either integrally formed at the distal end 32, soldered, or otherwise formed to the distal end of each primary lead 30. It is to be understood that when the distal end 32 is referred to as acting as an electrode, this is not limited to where the electrode 34 is integrally formed at the distal end 32. For example, the distal end can apply energy to the surrounding tissue where there is an electrode integrally formed at the distal end, or where an electrode is separately soldered to the distal end, or where there is another energy delivery device located at the distal end. The electrode 34 typically has a diameter greater than the diameter of the primary lead 30. For example, the primary lead 30 may have a diameter ranging from 0.18 mm (0.007 in.) to 0.28 mm (0.011 in.), while the electrode 34 has a diameter of 0.36 mm (0.014 in.) to 0.51 mm (0.020 in.). The primary leads 30 and the electrodes 34 are preferably made from a biologically-compatible material such as stainless steel. The insulation surrounding the primary leads 30 generally has a thickness of between 0.03 mm (0.001 in.) and 0.06 mm (0.0025 in.), resulting in a combined lead-insulation diameter of between 0.23 mm (0.009 in.) and 0.41 mm (0.016 in.). In an alternate configuration, as shown in FIGS. 2 and 3, each primary lead 30 is strip-shaped with a width from 0.76 mm (0.03 in.) to 1.0 mm (0.04 in) and a thickness of approximately 0.13 mm (0.005 in.), while the secondary lead 31 is typically tubular-shaped. It should be noted that these dimensions are provided for illustrative purposes, and not by way of limitation. A hemispherically shaped electrode 34 is formed at the distal end, as for example, by sanding down a sixteenth-inch (1.6 mm) diameter sphere which is soldered to the distal end 32 of the primary lead 30. The electrodes can also be constructed by stamping the desired shape or configuration from the conductive lead. The electrode is integral with the lead, and the remainder of the lead is insulated. The distal end 33 of the secondary lead 31 preferably includes a generally spherically-shaped electrode 35.

An alignment device 36 arranges the leads 30, 31 such that they are mounted to the catheter at only their proximal ends and so that separation is maintained between the leads within, and distal to the alignment device. The leads can form cantilevers when mounted on the alignment device. A preferred configuration of the alignment device 36 includes a plurality of off-center, axially-aligned lumina 38 which are substantially symmetrically positioned relative to the axis of the alignment device 36. The alignment device 36 is formed, for example, by extruding the plurality of axially-aligned lumina 38 through a solid cylinder composed of a dielectric material, such as polyamide. Each lead 30 passes through an individual off-center lumen 38 and exits out the rear of the alignment device 36. The alignment device 36 may further include a central lumen 48 that may be aligned with the axis. In some embodiments the central lumen 48 is used for accepting a guide wire or for the delivery or perfusion of medicant and cooling solution to the treatment area during application of RF energy. In other embodiments, the central lumen 48 may be used for the secondary lead 31. The alignment device 36 may also further include an auxiliary lumen 47 for additional leads, such as the leads of a thermocouple used as a temperature sensor. The alignment device 36 comprises a dielectric material to prevent or minimize any coupling effect the leads 30, 31 may have with each other and, if present, the guide wire. The length of the alignment device is, for example, 12.5 mm (0.5 in.) to 19.0 mm (0.75 in.) in one embodiment. However, these dimensions are provided for purposes of illustration and not by way of limitation.

In the embodiment of the invention shown in FIGS. 2, 2a and 3, the inner sheath 28 is attached to the alignment device 36 and extends beyond the rear 37 of the alignment device. Preferably, the inner sheath 28 completely surrounds the exterior wall of the alignment device 36 and is mounted to it by adhesive or press fit or in other manner such that it remains in a fixed position relative to the inner sheath. The inner sheath and alignment device can act as an inner member relative to the outer sheath. The inner sheath 28 comprises a biocompatible material with a low coefficient of friction. The inner sheath 28 provides a pathway for the interconnection between the leads 30, 31 and the electrical connector 18 (FIG. 1). This interconnection may occur in any of several ways. The leads 30, 31 themselves may be continuous and run the entire length of the inner sheath 28. In the alternative (not shown), the positively charged leads 30, 31 may couple with a common positively charged conductor housed in the inner sheath 28. Likewise, the negatively charged leads 30, 31 may couple with a common negative conductor. Preferably, the leads 30, 31 are connected to a conductor that allows for the polarity of the leads to be switched. The conductor may comprise, for example, a 36 gauge copper lead with a polyurethane coating. The coupling may occur at any point within the inner sheath 28. To reduce the amount of wire contained in the catheter, it is advantageous to couple the leads 30, 31 at the point where the leads exit the rear 37 of the alignment device 36. To add further stability to the electrode device 24, it is preferred that bonding material 40 surround the leads 30, 31 at the front end of the alignment device 36. In this embodiment, the leads 30, 31 exit through the distal orifice 14 as the outer sheath 12 is retracted backwards over the alignment device 36. The inwardly tapered tip 46 impedes the retracting movement of the outer sheath 12 to prevent the exposure of the alignment device 36.

FIG. 3 shows the leads 30 and 31 in the retracted position where all leads are within the nosecone-shaped tip portion 46 and the outer shell 44. The alignment device 36 has been moved relative to the outer shell 44. The soft nosecone provides an atraumatic tip for when the catheter is maneuvered through the tortuous venous system. The electrode at the distal end of the secondary lead 31 can be sized to approximately the same size as the opening formed in the nosecone 46. The nosecone forms a closed atraumatic tip together with the electrode of the secondary lead when the alignment device is retracted into the outer sheath of the catheter. This can present an atraumatic tip even where the nosecone is not constructed from a material having a soft durometer.

Referring now to FIGS. 4 and 5, in another embodiment, the alignment device 36 is attached to the outer sheath 12 and thereby remains immobile in relation to it. The inner sheath 28 is movably positioned at the rear of the alignment device 36 and again provides a pathway for the interconnection between the primary leads 30 and the electrical connector 18 (FIG. 1). In some embodiments the inner sheath 28 contains a guide-wire tube 49 that runs the entire length of the inner sheath. The guide-wire tube 49 is aligned to communicate with the central lumen 48 of the alignment device 36 at one end and with the guide-wire port 20 (FIG. 1) at the other end. The primary leads 30 may be continuous and run the entire length of the inner sheath 28 or they may be coupled to common leads as previously described. The primary leads 30 are secured to the front end 27 of the inner sheath 28, as for example with a potting material 50, so that the movement of the inner sheath 28 results in a corresponding movement of the primary leads 30 through the lumina 38 of the alignment device 36. In this embodiment, the primary leads 30 are not secured to the alignment device 36 and in essence are free-floating leads in the axial direction. The primary leads 30 travel through the alignment device 36 and exit through the distal orifice 14 as the front end of the inner sheath 28 is moved toward the rear 37 of the alignment device 36.

In the above embodiments, the primary leads 30 are formed, e. g., arced or bent, to move away from each other and thereby avoid contact. The "distal portion" of the primary leads 30 is the portion of the lead which extends from the front end of the alignment device 36 when the leads are fully extended through the distal orifice 14. It is preferred that the distal portions 42 are formed to move radially outward from each other relative to the axis of the alignment device 36 and form a symmetrical arrangement. This is shown in both the embodiments of FIG. 2a and FIG. 4a. The degree of arc or bend in the primary leads 30 may be any that is sufficient to radially expand the leads as they exit the outer sheath 12 through the distal orifice 14. It is essential that the degree of the arc or bend be sufficient to provide enough force so that the primary leads 30 expand through blood and the electrodes 34 come in apposition with the vein wall. The electrodes are preferably partially embedded in the vein wall to assure full contact. The rounded portion of the electrode is embedded into the vein wall to achieve full surface apposition so that the entire uninsulated surface area of the electrode is in contact with venous tissue for effective current distribution. The surface area of the electrodes in contact with the venous tissue preferably is sufficient to avoid a high current density which may lead to spot heating of the venous tissue. The heating effect is preferably distributed along a circumferential band of the vein. The apposed electrodes should be spaced no more than 4 or 5 millimeters from one another along the circumference of the vein. Thus, the electrode arrangement is related to the size or diameter of the vein being treated. Other properties of the primary leads 30, such as lead shape and insulation thickness, affect the push force of the lead and the degree of arc or bend must be adjusted to compensate for these factors. For example, in one configuration of the electrode device 24, a wire having a diameter of between 0.18 mm (0.007 in) and 0.28 mm (0.011 in) with a total insulation thickness of between 0.05 mm (0.002 in) to 0.13 mm (0.005 in) is arced or bent at an acute angle to provide sufficient apposition with the anatomical structure. It is to be understood that these dimensions are provided for illustrative purposes, and not by way of limitation.

Other techniques for expanding the leads outwardly once they have been extended from the working end of the catheter may be possible. For example, the leads may be straight but are mounted in the alignment device at an angle such that they are normally directed outward.

For increased appositional force, it is preferred that the primary leads 30 be strip-shaped, that is rectangular in cross section, with dimensions, for example, of a width from 0.76 mm (0.030 in.) to 1.0 mm (0.039 in) and a thickness of approximately 0.13 mm (0.005 in.). The rectangular cross section provides increased resistance to bending in the width dimension but allows bending more freely in the thickness dimension. This strip-shaped configuration of the primary leads 30 is shown in FIGS. 2, 2a, and 3 and provides for increased stability in the lateral direction while allowing the necessary bending in the radial direction. In FIGS. 2, 2a, and 3, each primary lead comprises a rectangular cross section mounted in relation to the catheter such that the thinner dimension of the rectangular cross section is aligned with the direction of expansion of the lead. The leads are less likely to bend sideways when expanded outward, and a uniform spacing between leads is more assured. Uniform spacing promotes uniform heating around the venous tissue which is in apposition with the electrodes at the distal ends of the leads.

The length of the distal portion of the leads 30 also affects the configuration of the electrode device 24. The maximum distance between two mutually opposed electrodes 34; i.e., the effective diameter of the electrode device 24, is affected by the bend degree and length of the distal portion 42. The longer the length of the distal portion 42 the greater the diameter of the electrode device 24. Accordingly, by changing the distal portion 42 length and arc or bend degree, the catheter 10 can be configured for use in differently sized anatomical structures.

Different numbers of leads 30, 31 can be employed with the catheter. The number of leads 30, 31 is limited by the diameter of the alignment device 36 and the number of lumina 36, 38, 47 that can be extruded through the alignment device. In a bipolar configuration, an even number of primary leads 30 are preferably available to form a number of oppositely charged electrode pairs. The electrodes in appostion with the anatomical structure should be maintained within a certain distance of each other. In a monopolar configuration, any number of commonly charged leads 30 can be present. In the monopolar mode, distribution of RF energy through the anatomical tissue is obtained by creating a return path for current through the tissue by providing a return device at a point external from the tissue, such as a large metal pad.

Now referring again to FIG. 1, an actuator 25 controls the extension of the electrode device 24 through the distal orifice 14. The actuator 25 may take the form of a switch, lever, threaded control knob, or other suitable mechanism, and is preferably one that can provide fine control over the movement of the outer sheath 12 or the inner sheath 28, as the case may be. In one embodiment of the invention, the actuator 25 (FIG. 1) interfaces with the outer sheath 12 (FIG. 2, 2a and 3) to move it back and forth relative to the inner sheath 28. In another embodiment the actuator 25 (FIG. 1) interfaces with the inner sheath 28 (FIGS. 4, 4a and 5) to move it back and forth relative to the outer sheath 12. The relative position between the outer sheath and inner sheath is thus controlled, but other control approaches may be used.

Referring again to FIGS. 2, 2a, 3, 4, 4a and 5, the catheter 10 includes a temperature sensor 26, such as a thermocouple. The temperature sensor 26 is mounted in place on an electrode 34 so that the sensor 26 is nearly or is substantially flush with the exposed surface of the electrode 34. The sensor 26 is shown in the drawings as protruding from the electrodes for clarity of illustration only. The sensor 26 senses the temperature of the portion of the anatomical tissue that is in apposition with the exposed electrode surface. Monitoring the temperature of the anatomical tissue provides a good indication of when shrinkage of the tissue is ready to begin. A temperature sensor 26 placed on the electrode facing the anatomical tissue provides an indication of when shrinkage occurs (70° C. or higher) and when significant amounts of heat-induced coagulum may begin to form on the electrodes (at 85° C. or higher). Therefore maintaining the temperature above 70 degrees Centigrade produces a therapeutic shrinkage of the anatomical structure. Application of the RF energy from the electrodes 34 is halted or reduced when the monitored temperature reaches or exceeds the specific temperature that was selected by the operator, typically the temperature at which anatomical tissue begins to cauterize. The temperature sensor 26 interfaces with the controller 23 (FIG. 1) through a pair of sensor leads 45 which preferably run through the auxiliary lumen 47 and then through the inner sheath 28. The signals from the temperature sensor 26 are provided to the controller 23 which controls the magnitude of RF energy supplied to the electrodes 34 in accordance with the selected temperature criteria and the monitored temperature. Other techniques such as impedance monitoring, and ultrasonic pulse echoing can be utilized in an automated system which shuts down or regulates the application of RF energy from the electrodes to the venous section when sufficient shrinkage of the vein is detected and to avoid overheating the vein.

Referring now to FIGS. 6, 6*a* and 7*a* through 7*c*, in the operation of one embodiment of the catheter 10, the catheter is inserted into a hollow anatomical structure, such as a vein 52. The catheter is similar to the embodiment discussed in connection with FIGS. 2 and 3. The catheter 10 further includes an external sheath 60 through which a fluid can be delivered to the treatment site. In this embodiment, the fluid port (not shown) communicates with the interior of the external sheath 60, and fluid is delivered from between the external sheath 60 and the outer sheath 12. The external sheath 60 surrounds the outer sheath 12 to form a coaxial channel through which fluid may be flushed.

Fluoroscopy, ultrasound, an angioscope imaging technique, or other technique may be used to direct the specific placement of the catheter and confirm the position in the vein. The actuator (not shown) is then operated to shift the outer sheath relative to the inner sheath by either retracting the outer sheath 12 backward or advancing the inner sheath 28 forward to expose the leads 30, 31 through the distal orifice 14. As the leads 30, 31 exit the distal orifice 14, the primary leads 30 expand radially outward relative to the axis of the alignment device 36, while the secondary lead 31 remains substantially linear. The primary leads 30 continue to move outward until apposition with the vein wall 54 occurs and the outward movement of the primary leads 30 is impeded. The primary leads 30 contact the vein along a generally circumferential band of the vein wall 54. This outward movement of the primary leads 30 occurs in a substantially symmetrical fashion. As a result, the primary-lead electrodes 34 are substantially evenly spaced along the circumferential band of the vein wall 54. The central-lead electrode 35 is suspended within the vein 52 without contacting the vein wall 54.

When the electrodes 34 are positioned at the treatment site of the vein, the power supply 22 is activated to provide suitable RF energy, preferably at a selected frequency from a range of 250 kHz to 350 MHZ. One suitable frequency is 510 kHz. One criterion used in selecting the frequency of the energy to be applied is the control desired over the spread, including the depth, of the thermal effect in the venous tissue. Another criterion is compatibility with filter circuits for eliminating RF noise from thermocouple signals.

In bipolar operation, the primary leads 30 are initially charged such that adjacent leads are oppositely charged while the secondary lead is electrically neutral. These multiple pairs of oppositely charged leads 30 form active electrode pairs to produce an RF field between them. Thus, discrete RF fields are set up along the circumferential band of the vein wall 54. These discrete fields form a symmetrical RF field pattern along the entire circumferential band of the vein wall 54, as adjacent electrodes 34 of opposite polarity produce RF fields between each other. A uniform temperature distribution can be achieved along the vein wall being treated.

The RF energy is converted within the adjacent venous tissue into heat, and this thermal effect causes the venous tissue to shrink, reducing the diameter of the vein. A uniform temperature distribution along the vein wall being treated avoids the formation of hot spots in the treatment area while promoting controlled uniform reduction in vein diameter. The thermal effect produces structural transfiguration of the collagen fibrils in the vein. The collagen fibrils shorten and thicken in cross-section in response to the heat from the thermal effect. As shown in FIG. 7*a*, the energy causes the vein wall 54 to collapse around the primary-lead electrodes 34. The wall 54 continues to collapse until further collapse is impeded by the electrodes 34. The electrodes are pressed farther and farther together by the shrinking vein wall 54 until they touch and at that point, further collapse or ligation of the wall 54 is impeded. Upon collapse of the vein wall 54 around the primary-lead electrodes 34, the polarity of the primary-lead electrodes is switched so that all primary-lead electrodes are commonly charged. The switching of polarity for the leads need not be instantaneous. The application of RF energy can be ceased, the polarity switched, and then RF energy is applied again at the switched polarity. The secondary-lead electrode 35 is then charged so that its polarity is opposite that of the primary-lead electrodes 34. The RF field is set up between the primary-lead electrodes 34 and the secondary-lead electrode 35.

The catheter 10 is then pulled back while energy is applied to the electrode device. As shown in FIG. 7*b*, while the catheter 10 is being pulled back, the primary-lead electrodes 34 remain in apposition with the vein wall 54 while the secondary-lead electrode 35 comes in contact with the portion of the vein wall previously collapsed by the primary-lead electrodes 34. Accordingly, RF energy passes through the vein wall 54 between the primary-lead electrodes 34 and the secondary-lead electrode 35 and the vein wall continues to collapse around the secondary-lead electrode 35 as the catheter 10 is being retracted. As shown in FIG. 7*c*, ligation in accordance with this method results in an occlusion along a length of the vein 52. A lengthy occlusion, as opposed to an acute occlusion, is stronger and less susceptible to recanalization.

A similar result is achieved when the catheter 10 having both primary and secondary leads is operated in a monopolar manner. In a monopolar operation, the secondary-lead electrode 35 remains neutral, while the primary leads 30 are commonly charged and act in conjunction with an independent electrical device, such as a large low-impedance return pad (not shown) placed in external contact with the body, to form a series of discrete RF fields. These RF fields are substantially evenly spaced around the circumference of the vein and travel along the axial length of the vein wall causing the vein wall to collapse around the primary-lead electrodes. Upon collapse of the vein wall, the secondary-lead electrode is charged to have the same polarity as that of the primary-lead electrodes. The electrode device is retracted and the vein wall collapses as described in the bipolar operation.

In either bipolar or monopolar operation the application of RF energy is substantially symmetrically distributed through the vein wall, regardless of the diameter of the vein 52. This symmetrical distribution of RF energy increases the predictability and uniformity of the shrinkage and the strength of the occlusion. Furthermore, the uniform distribution of energy allows for the application of RF energy for a short duration and thereby reduces or avoids the formation of heat-induced coagulum on the electrodes 34. The leads, including the non-convex outer portion of the electrode, are insulated to further prevent heating of the surrounding blood.

Fluid can be delivered before and during RF heating of the vein being treated through a coaxial channel formed between the external sheath 60 and the outer sheath 12. It is to be understood that another lumen can be formed in the catheter to deliver fluid to the treatment site. The delivered fluid displaces or exsanguinates blood from the vein so as to avoid heating and coagulation of blood. Fluid can continue to be delivered during RF treatment to prevent blood from circulating back to the treatment site. The delivery of a dielectric fluid increases the surrounding impedance so that RF energy is directed into the tissue of the vein wall.

Referring now to FIGS. 8, 8a, 9a and 9b, in the operation of an alternate embodiment of the catheter 10 that may be used with a guide wire 53. As in the previous embodiment, the catheter 10 is inserted into a hollow anatomical structure, such as a vein 52. The guide wire 53 is advanced past the point where energy application is desired. The catheter 10 is then inserted over the guide wire 53 by way of the central lumen 48 and the guide wire tube 49 (FIG. 4) and is advanced over the guide wire through the vein to the desired point. The guide wire 53 is typically pulled back or removed before RF energy is applied to the electrode device 24.

The actuator 25 (FIG. 1) is then manipulated to either retract the outer sheath 12 backward, or advance the inner sheath 28 forward to expose the leads 30 through the distal orifice 14. The leads 30 exit the distal orifice 14 and expand radially outward relative to the axis of the alignment device 36. The leads 30 continue to move outward until apposition with the vein wall 54 occurs. The leads 30 contact the vein along a generally circumferential band of the vein wall 54. This outward movement of the leads occurs in a substantially symmetrical fashion. As a result, the electrodes 34 are substantially evenly spaced along the circumferential band of the vein wall 54. Alternately, the electrodes can be spaced apart in a staggered fashion such that the electrodes do not lie along the same plane. For example, adjacent electrodes can extend different lengths from the catheter so that a smaller cross-sectional profile is achieved when the electrodes are collapsed toward one another.

When the electrodes 34 are positioned at the treatment site of the vein, the power supply 22 is activated to provide suitable RF energy to the electrodes 34 so that the catheter 10 operates in either a bipolar or monopolar manner as previously described. As shown in FIGS. 9a and 9b, the energy causes the vein wall 54 to collapse around the electrodes 34 causing the leads to substantially straighten and the electrodes to cluster around each other. The wall 54 continues to collapse until further collapse is impeded by the electrodes 34 (FIG. 9b). At this point the application of energy may cease. The electrodes can be configured to form a shape with a reduced profile when collapsed together. The electrodes can also be configured and insulated to continue applying RF energy after forming a reduced profile shape by the collapse of the vein wall. The catheter 10 can be pulled back to ligate the adjacent venous segment. If a temperature sensor 26 is included, the application of energy may cease prior to complete collapse if the temperature of the venous tissue rises above an acceptable level as defined by the controller 23.

Where the catheter includes a fluid delivery lumen (not shown), fluid can be delivered before and during RF heating of the vein being treated. The fluid can displace blood from the treatment area in the vein to avoid the coagulation of blood. The fluid can be a dielectric medium. The fluid can include an anticoagulant such as heparin which can chemically discourage the coagulation of blood at the treatment site.

After completing the procedure for a selected venous section, the actuator mechanism causes the primary leads to return to the interior of the outer sheath 12. Either the outer sheath or the inner sheath is moved to change the position of the two elements relative to one another. Once the leads 30 are within the outer sheath 12, the catheter 10 may be moved to another venous section where the ligation process is repeated. Upon treatment of all venous sites, the catheter 10 is removed from the vasculature. The access point of the vein is then sutured closed, or local pressure is applied until bleeding is controlled.

Another embodiment of the catheter is illustrated in FIG. 10. The inner member or sheath 28 is contained within the outer sheath 12. The inner sheath is preferably constructed from a flexible polymer such as polyimide, polyethylene, or nylon, and can travel the entire length of the catheter. The majority of the catheter should be flexible so as to navigate the tortuous paths of the venous system. A hypotube having a flared distal end 33 and a circular cross-sectional shape is attached over the distal end of the inner sheath 28. The hypotube is preferably no more than about two to three centimeters in length. The hypotube acts as part of the conductive secondary lead 31. An uninsulated conductive electrode sphere 35 is slipped over the hypotube. The flared distal end of the hypotube prevents the electrode sphere from moving beyond the distal end of the hypotube. The sphere is permanently affixed to the hypotube, such as by soldering the sphere both front and back on the hypotube. The majority or the entire surface of the spherical electrode 35 remains uninsulated. The remainder of the hypotube is preferably insulated so that the sphere-shaped distal end can act as the electrode. For example, the hypotube can be covered with an insulating material such as a coating of parylene. The interior lumen of the hypotube is lined by the inner sheath 28 which is attached to the flaired distal end of the hypotube by adhesive such as epoxy.

Surrounding the secondary lead 31 and sphere-shaped electrode 35 are a plurality of primary leads 30 which preferably have a flat rectangular strip shape and can act as arms. As illustrated in FIG. 11, the plurality of primary leads are preferably connected to common conductive rings 62. This configuration maintains the position of the plurality of primary leads, while reducing the number of internal electrical connections. The rings 62 are attached to the inner sheath 28. The position of the rings and the primary leads relative to the outer sheath follows that of the inner sheath. As earlier described, the hypotube of the secondary lead 31 is also attached to the inner sheath 28. Two separate conductive rings can be used so that the polarity of different primary leads can be controlled separately. For example, adjacent primary leads can be connected to one of the two separate conductive rings so that the adjacent leads can be switched to have either opposite polarities or the same polarity. The rings are preferable spaced closely together, but remain electrically isolated from one another along the inner sheath. Both the rings and the hypotube are coupled with the inner sheath, and the primary leads 30 that are connected to the rings move together with and secondary lead while remaining electrically isolated from one another.

Epoxy or another suitable adhesive can be used to attach the rings to the inner sheath. The primary leads from the respective rings each alternate with each other along the circumference of the inner sheath. The insulation along the underside of the leads prevents an electrical short between the rings.

The ring and primary leads are attached together to act as cantilevers where the ring forms the base and the rectangular primary leads operate as the cantilever arms. The leads 30 are connected to the ring and are formed to have an arc or bend such that the leads act as arms which tend to spring outwardly away from the catheter and toward the surrounding venous tissue. Insulation along the underside of the leads and the rings prevents unintended electrical coupling between the leads and the opposing rings. Alternately, the leads are formed straight and connected to the ring at an angle, such that the leads tend to expand or spring radially outward from the ring. The angle at which the leads are attached to the ring should be sufficient to force the primary distal ends and electrodes 34 through blood and into apposition with the vein wall. Other properties of the primary leads 30, such as lead shape and insulation thickness, affect the push force of the lead and the degree of arc or bend must be adjusted to compensate for these factors. The rectangular cross section of the leads 30 can provide increased stability in the lateral direction while allowing the necessary bending in the radial direction. The leads 30 are less likely to bend sideways when expanded outward, and a uniform spacing between leads is more assured. Uniform spacing between the leads 30 and the distal ends promotes uniform heating around the vein by the electrodes 34.

The distal ends of the primary leads 30 are uninsulated to act as electrodes 34 having a spoon or hemispherical shape. The leads can be stamped to produce an integral shaped electrode at the distal end of the lead. The uninsulated outer portion of the distal end electrode 34 which is to come into apposition with the wall of the anatomical structure is preferably rounded and convex. The flattened or non-convex inner portion of the distal end is insulated to minimize any unintended thermal effect, such as on the surrounding blood in a vein. The distal end electrodes 34 are configured such that when the distal ends are forced toward the inner sheath 12, as shown in FIG. 10a, the distal ends combine to form a substantially spherical shape with a profile smaller than the profile for the spherical electrode 35 at the secondary distal end.

The outer sheath 12 can slide over and surround the primary and secondary leads 30, 31. The outer sheath 12 includes an orifice which is dimensioned to have approximately the same size as the spherical electrode 35 at the secondary distal end which functions as an electrode. A close or snug fit between the electrode 35 at the secondary distal end and the orifice of the outer sheath 12 is achieved. This configuration provides an atruamatic tip for the catheter. The electrode 35 secondary distal end is preferably slightly larger than the orifice. The inner diameter of the outer sheath 12 is approximately the same as the reduced profile of the combined primary distal end electrodes 34. The diameter of the reduced profile of the combined primary distal end electrodes 34 is preferably less than the inner diameter of the outer sheath.

A fluid port (not shown) can communicate with the interior of the outer sheath 12 so that fluid can be flushed between the outer sheath 12 and the inner sheath 28. Alternately, a fluid port can communicate with a central lumen 48 in the hypotube which can also accept a guidewire. As previously stated, the catheter 10 can be periodically flushed with saline which can prevent the buildup of biological fluid, such as blood, within the catheter 10. A guide wire can be introduced through the lumen 48 for use in guiding the catheter to the desired treatment site. As previously described, a fluid can be flushed or delivered though the lumen as well. If a central lumen is not desired, the lumen of the hypotube can be filled with solder.

Preferably, the primary leads 30 and the connecting rings are connected to a power source 22 such that the polarity of the leads may be switched as desired. This allows for the electrode device 24 to operate in either a bipolar or a monopolar configuration. When adjacent primary leads 30 have opposite polarity, a bipolar electrode operation is available. When the primary leads 30 are commonly charged a monopolar electrode operation is available in combination with a large return electrode pad placed in contact with the patient. When the primary leads 30 are commonly charged, and a secondary lead 31 has an opposite polarity, a bipolar electrode operation is available. More or fewer leads may be used. The number of leads can be dependent on the size or diameter of the hollow anatomical structure to be treated.

Although not shown, it is to be understood that the catheter 10 can include a temperature sensor, such as a thermocouple, mounted in place on the distal end or electrode 34 so that the sensor is substantially flush with the exposed surface of the electrode 34. The sensor senses the temperature of the portion of the anatomical tissue that is in apposition with the exposed electrode surface. Application of the RF energy from the electrodes 34 is halted or reduced when the monitored temperature reaches or exceeds the specific temperature that was selected by the operator, such as the temperature at which anatomical tissue begins to cauterize. Other techniques such as impedance monitoring, and ultrasonic pulse echoing can be utilized in an automated system which shuts down or regulates the application of RF energy from the electrodes to the venous section when sufficient shrinkage of the vein is detected and to avoid overheating the vein.

Figure 12:
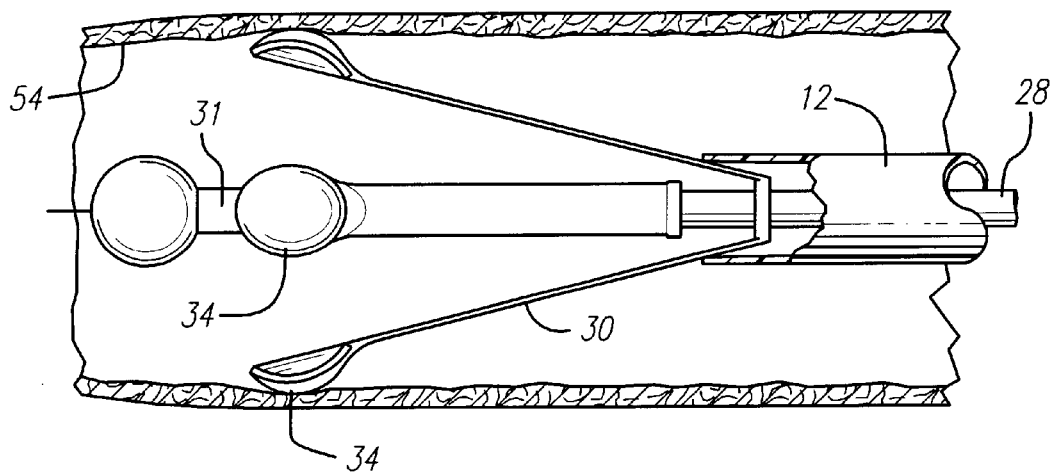
FIG. 12 is a cross-sectional view of an anatomical structure containing the catheter of FIG. 10 with the electrodes in apposition with the anatomical structure.
Figure 13:
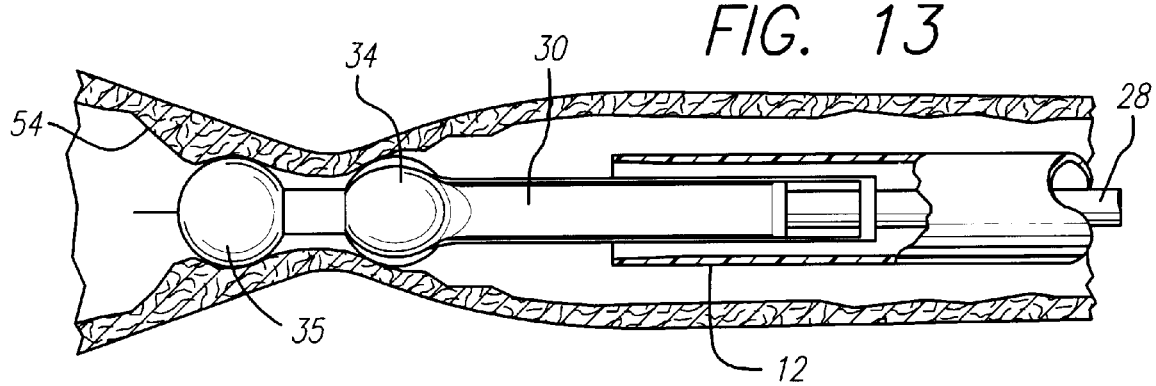
FIG. 13 is a cross-sectional view of the anatomical structure containing the catheter of FIG. 10 where the anatomical structure is being ligated by the application of energy from the electrodes.
Figure 14:
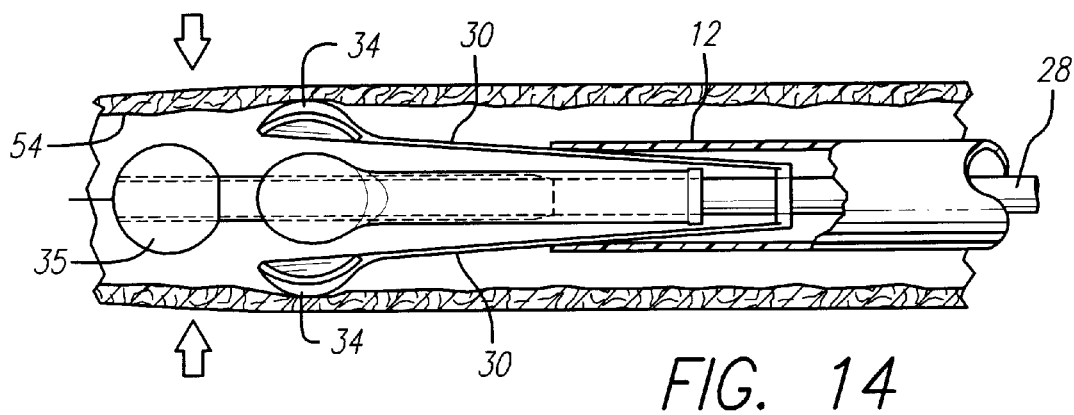
FIG. 14 is a cross-sectional view of an anatomical structure containing the catheter of FIG. 10 with the electrodes in apposition with the anatomical structure where external compression is being applied to reduce the diameter of the hollow structure before the application of energy from the electrodes to ligate the structure.

Referring now to FIGS. 12 through 14, in the operation of one embodiment of the catheter 10, the catheter is inserted into a hollow anatomical structure, such as a vein. Fluoroscopy, ultrasound, an angioscope imaging technique, or another technique may be used to direct and confirm the specific placement of the catheter in the vein. The actuator is then operated to retract the outer sheath 12 to expose the leads 30, 31. As the outer sheath no longer restrains the leads, the primary leads 30 move outward relative to the axis defined by the outer sheath, while the secondary lead 31 remains substantially linear along the axis defined by the outer sheath. The primary leads 30 continue to move outward until the distal end electrode 34 of the primary leads are placed in apposition with the vein wall 54 occurs and the outward movement of the primary leads 30 is impeded. The primary leads 30 contact the vein along a generally circumferential area of the vein wall 54. This outward movement of the primary leads 30 occurs in a substantially symmetrical fashion so that the primary distal end electrodes 34 are substantially evenly spaced. The central-lead electrode 35 is suspended within the vein without contacting the vein wall 54.

When the electrodes 34 are positioned at the treatment site of the vein, the power supply 22 is activated to provide suitable RF energy. In a bipolar operation, the primary leads 30 are initially charged such that adjacent leads are oppositely charged while the secondary lead is electrically neutral. These multiple pairs of oppositely charged leads 30 form active electrode pairs to produce an RF field between them, and form a symmetrical RF field pattern along a circumferential band of the vein wall to achieve a uniform temperature distribution along the vein wall being treated.

The RF energy produces a thermal effect which causes the venous tissue to shrink, reducing the diameter of the vein. As shown in FIG. 13, the energy causes the vein wall 54 to collapse until further collapse is impeded by the electrodes 34. The electrodes are pressed closer together by the shrinking vein wall. The electrodes 34 are pressed together to assume a reduced profile shape which is sufficiently small so that the vein is effectively ligated. Upon collapse of the vein wall 54 around the primary-lead electrodes 34, the polarity of the primary-lead electrodes is switched so that all of the primary-lead electrodes are commonly charged. The secondary-lead electrode 35 is then charged so that its polarity is opposite that of the primary-lead electrodes 34. Where the primary electrodes 34 and the secondary electrode 35 are spaced sufficiently close together, when the vein wall collapses around the primary lead electrodes, the electrode at the distal end of the secondary lead can also come into contact with the a portion of the vein wall so that an RF field is created between the primary electrodes 34 and the secondary electrode 35.

The catheter 10 is pulled back to ensure apposition between the electrodes at the distal ends of the leads and the vein wall. When the catheter 10 is being pulled back, the primary-lead electrodes 34 remain in apposition with the vein wall 54 while the secondary-lead electrode 35 comes in contact with the portion of the vein wall previously collapsed by the primary-lead electrodes 34. RF energy passes through the venous tissue between the primary-lead electrodes 34 and the secondary-lead electrode 35. Ligation as the catheter is being retracted produces a lengthy occlusion which is stronger and less susceptible to recanalization than an acute point occlusion.

In a monopolar operation, the secondary-lead electrode 35 remains neutral, while the primary leads 30 are commonly charged and act in conjunction with an independent electrical device, such as a large low-impedance return pad (not shown) placed in external contact with the body, to form RF fields substantially evenly spaced around the circumference of the vein. The thermal effect produced by those RF fields along the axial length of the vein wall causes the vein wall to collapse around the primary-lead electrodes. Upon collapse of the vein wall, the secondary-lead electrode is charged to have the same polarity as that of the primary-lead electrodes. The electrode device is retracted as described in the bipolar operation.

In either bipolar or monopolar operation the application of RF energy is substantially symmetrically distributed through the vein wall. As previously described, the electrodes should be spaced no more than 4 or 5 millimeters apart along the circumference of the vein, which defines the target vein diameter for a designed electrode catheter. Where the electrodes are substantially evenly spaced in a substantially symmetrical arrangement, and the spacing between the electrodes is maintained, a symmetrical distribution of RF energy increases the predictability and uniformity of the shrinkage and the strength of the occlusion.

As shown in FIG. 14, after the electrodes 34 come into apposition with the vein wall (FIG. 12), and before the energy is applied to ligate the vein (FIG. 13), an external tourniquet, such as an elastic compressive wrap or an inflatable bladder with a window transparent to ultrasound, is used to compress the anatomy, such as a leg, surrounding the structure to reduce the diameter of the vein. Although the compressive force being applied by the tourniquet may effectively ligate the vein, or otherwise occlude the vein by flattening the vein, for certain veins, this compressive force will not fully occlude the vein. A fixed diameter electrode catheter in this instance would not be effective. The electrodes 34 which are expanded outward by the formed leads 30 can accommodate this situation.

The reduction in vein diameter assists in pre-shaping the vein to prepare the vein to be molded to a ligated state. The use of an external tourniquet also exsanguinates the vein and blood is forced away from the treatment site. Coagulation of blood during treatment can be avoided by this procedure. Energy is applied from the electrodes to the exsanguinated vein, and the vein is molded to a sufficiently reduced diameter to achieve ligation. The external tourniquet can remain in place to facilitate healing.

The catheter can be pulled back during the application of RF energy to ligate an extensive section of a vein. In doing so, instead of a single point where the diameter of the vein has been reduced, an extensive section of the vein has been painted by the RF energy from the catheter. Retracting the catheter in this manner produces a lengthy occlusion which is less susceptible to recanalization. The combined use of the primary and secondary electrodes can effectively produce a reduced diameter along an extensive length of the vein. The catheter can be moved while the tourniquet is compressing the vein, of after the tourniquet is removed.

Where the catheter includes a fluid delivery lumen, fluid can be delivered to the vein before RF energy is applied to the vein. The delivered fluid displaces blood from the treatment site to ensure that blood is not present at the treatment site, even after the tourniquet compresses the vein.

Where the tourniquet is an inflatable bladder with a window transparent to ultrasound, an ultrasound transducer is used to monitor the flattening or reduction of the vein diameter from the compressive force being applied by the inflating bladder. The window can be formed from polyurethane, or a stand-off of gel contained between a polyurethane pouch. A gel can be applied to the window to facilitate ultrasound imaging of the vein by the transducer. Ultrasound visualization through the window allows the operator to locate the desired venous treatment area, and to determine when the vein has been effectively ligated or occluded. Ultrasound visualization assists in monitoring any pre-shaping of the vein in preparation of being molded into a ligated state by the thermal effect produced by the RF energy from the electrodes.

After completing the procedure for a selected venous section, the actuator causes the leads 30 to return to the interior of the outer sheath 12. Once the leads 30 are within the outer sheath 12, the catheter 10 may be moved to another venous section where the ligation process is repeated.

The description of the component parts discussed above are for a catheter to be used in a vein ranging in size from 2 mm (0.08 in) to 10 mm (0.4 in) in diameter. It is to be understood that these dimensions do not limit the scope of the invention and are merely exemplary in nature. The dimensions of the component parts may be changed to configure a catheter 10 that may used in various-sized veins or other anatomical structures.

Although described above as positively charged, negatively charged, or as a positive conductor or negative conductor, these terms are used for purposes of illustration only. These terms are generally meant to refer to different electrode potentials and are not meant to indicate that any particular voltage is positive or negative. Furthermore, other types of energy such as light energy from fiber optics can be used to create a thermal effect in the hollow anatomical structure undergoing treatment.

While several particular forms of the invention have been illustrated and described, it will be apparent that various modifications can be made without departing from the spirit and scope of the invention. Accordingly, it is not intended that the invention be limited, except as by the appended claims.

What is claimed is:

1. An apparatus for applying energy from a power source to a hollow anatomical structure having an inner wall, the apparatus comprising:

a catheter having a working end with a distal tip with an orifice formed therein;

a plurality of leads disposed at the working end, each lead having a distal portion with an uninsulated distal end, each lead electrically connected to the power source;

means for extending the leads through the distal orifice; and means for expanding the leads outwardly into non-penetrating contact with the inner wall when the leads have been extended;

whereby the leads move away from each other and into contact with the anatomical structure when extended out the distal orifice.

2. The apparatus of claim 1 wherein the leads are disposed in relation to the working end such that the distal portions of the leads move away from each other when extended through the distal orifice to form a substantially symmetric arrangement of substantially evenly spaced distal ends.

3. The apparatus of claim 2 wherein the leads are disposed in relation to the working end such that when the leads are extended through the distal orifice, the distance between two mutually opposed distal ends is greater than the diameter of the working end.

4. The apparatus of claim 1 wherein the distal end of each lead includes a hemispherical shape having an uninsulated rounded convex surface, wherein the remainder of the hemispherical shape is insulated.

5. The apparatus of claim 4 wherein the leads are mounted at the working end in a cantilever arrangement.

6. The apparatus of claim 1 wherein the extending means include a conductive ring, and at least one of the leads is connected the ring, and the conductive ring is connected to a power source.

7. The apparatus of claim 1 wherein the expansion means include a bend formed in each lead such that each lead tends to move outward away from the other leads.

8. The apparatus claim 7 wherein the expansion means include a bend formed with an angle less than ninety degrees for each lead.

9. The apparatus of claim 1 wherein each lead comprises a rectangular cross section mounted in relation to the catheter such that the thinner dimension of the rectangular cross section is aligned with the direction of expansion of the lead.

10. The apparatus of claim 1 further comprising a secondary lead connected to the extending means, the secondary lead having a distal end and a length such that the distal end of the secondary lead extends past the distal end of the leads, wherein the extending means extends the leads and the secondary lead through the distal orifice.

11. The apparatus of claim 10 further comprising a spherically shaped electrode mounted at the distal end of the secondary lead.

12. The apparatus of claim 10 further comprising:

a controller that controls the output of the power source to the leads and the secondary lead;

wherein the controller is adapted to switch the electrical polarity of the distal ends of the leads to a common polarity and switch the polarity of the secondary lead to a polarity opposite that of the leads.

13. The apparatus of claim 10 wherein the secondary lead is centrally located with respect to the leads.

14. The apparatus of claim 10 wherein the secondary lead includes a guide wire lumen for receiving a guide wire.

15. The apparatus of claim 1 wherein the extending means comprise:

an outer sheath mounted on the catheter, the outer sheath being movable; and an alignment device positioned inside the outer sheath, the alignment device maintaining separation between the leads;

wherein movement of the outer sheath in relation to the alignment device extends the leads through the orifice.

16. The apparatus of claim 1 wherein the extension means comprise:

an outer sheath mounted on the catheter;

an alignment device positioned inside the outer sheath, the leads being mounted to the alignment device such that the alignment device maintains separation between the leads;

a movable inner sheath to which the leads are attached, the inner sheath being movable in relation to the outer sheath;

wherein movement of the inner sheath in relation to the outer sheath extends the leads through the orifice.

17. The apparatus of claim 1 further comprising a switch connected to the power source, wherein the leads are adapted to be electrically connected to the power source, and the polarity of the leads are selectively changed by the switch.

18. The apparatus of claim 1 further comprising:

a controller that controls the power source; and a temperature sensor mounted to a distal end of a lead, the temperature sensor providing temperature signals to the controller;

wherein the controller controls the power source in response to signals from the temperature sensor.

19. The apparatus of claim 1 wherein the leads are formed and mounted to the catheter such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it.

20. The apparatus of claim 1 wherein the distal end of the leads each include a rounded convex surface which is uninsulated.

21. The apparatus of claim 1 wherein the catheter comprises a lumen having an opening at the working end and is configured to conduct fluid such as drugs, dielectric fluid, heparin, or saline, through the catheter.

22. The apparatus of claim 21 wherein the lumen is centrally located in the catheter and is also adapted to receive a guide wire.

23. The apparatus of claim 21 wherein the lumen is located between an inner and outer sheath in the catheter.

24. An apparatus for applying energy from a power source to an inner wall of a hollow anatomical structure, the apparatus comprising:
- a catheter having a working end with a distal tip with an orifice formed therein;
- a plurality of leads disposed at the working end, each lead having an uninsulated distal end, each lead electrically connected to the power source and each lead mounted at a proximal end to the working end in a cantilever arrangement; and
- means for extending the leads through the distal orifice;
- wherein each lead comprises a bend formed in the lead such that when the leads have been extended through the orifice, the leads expand outwardly moving away from each other into non-penetrating contact with the inner wall to form a substantially symmetric arrangement of substantially evenly spaced distal ends.

25. The apparatus of claim 24 wherein each lead comprises an electrode mounted at its distal end, the electrode having a hemispherical shape.

26. The apparatus of claim 24 wherein each lead comprises an electrode mounted at its distal, the electrode having a spherical shape.

27. The apparatus of claim 24 wherein each lead comprises a rectangular cross section mounted in relation to the catheter such that the thinner dimension of the rectangular cross section is aligned with the direction of expansion of the lead.

28. The apparatus of claim 24 further comprising a secondary lead mounted to the working end, the secondary lead having a distal end and a length exceeding that of the leads, the extension means also for extending the secondary lead through the distal orifice.

29. The apparatus of claim 28 further comprising a spherically shaped electrode mounted at the distal end of the secondary lead.

30. The apparatus of claim 28 further comprising:
- a controller that controls the output of the power source to the electrodes of the leads and the secondary lead;
- wherein the controller is adapted to switch the electrical polarity of the distal ends of the leads to a common polarity and switch the polarity of the secondary lead to a polarity opposite that of the leads.

31. The apparatus of claim 28 wherein the secondary lead is centrally located with respect to the leads.

32. The apparatus of claim 24 wherein the leads are formed and mounted to the catheter such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it.

33. The apparatus of claim 24 wherein the distal end of the leads each include a rounded convex surface which is uninsulated.

34. The apparatus of claim 24 wherein the catheter comprises a lumen having an opening at the working end and is configured to conduct fluid such as drugs, dielectric fluid, heparin, or saline, through the catheter.

35. The apparatus of claim 34 wherein the lumen is centrally located in the catheter and is also adapted to receive a guide wire.

36. The apparatus of claim 34 wherein the lumen is located between an inner and outer sheath in the catheter.

37. An apparatus for delivering energy to ligate an anatomical structure, the anatomical structure having an inner wall, the apparatus comprising:
- a catheter having a sheath, a working end, and an opening formed at the working end of the catheter;
- an inner member disposed within the sheath such that the inner member and the sheath are capable of being moved relative to one another;
- a plurality of leads, each lead having a distal end, the plurality of leads being attached to the inner member such that the distal ends of the plurality of leads extend out of the opening at the working end of the catheter when the position of the sheath changes in one direction relative to the inner member, each lead being formed to move the distal end away from a longitudinal axis defined by the sheath when the plurality of leads are extended out the opening and into non-penetrating apposition with the inner wall of the hollow anatomical structure;
- wherein the distal ends of the leads are configured to deliver energy to the inner wall of the anatomical structure.

38. The apparatus of claim 37, further comprising an actuation mechanism located remotely from the working end of the catheter, the actuation mechanism being coupled to the sheath and the inner member such that an operator manually controls the movement of the sheath and the inner member relative to one another.

39. The apparatus of claim 38, wherein the actuation mechanism is coupled to the sheath such that the sheath is moved relative to the inner member.

40. The apparatus of claim 38, wherein the actuation mechanism is coupled to the inner member such that the inner member is moved relative to the sheath.

41. The apparatus of claim 46, wherein the anatomical structure is a vein, and the leads are formed and mounted to the inner member such that when in an unconfined configuration, the leads have sufficient strength to move themselves outward into non-penetrating apposition with the vein wall, and further, the leads are formed and mounted to the inner member such that they do not have sufficient strength to prevent the reduction of the diameter of the vein wherein as the vein wall reduces, the leads remain in non-penetrating apposition with the vein wall and move inward with it.

42. The apparatus of claim 37, further comprising a secondary lead having a distal secondary end, the secondary lead being attached with the inner member such that the distal secondary end of secondary lead is extended out of the opening at the working end of the catheter when the position of the inner member changes in one direction relative to the sheath, wherein the distal ends of the leads are located between the distal secondary end of the secondary lead and the inner member.

43. The apparatus of claim 42, wherein the leads are electrically connected to a power source such that the polarity of each lead can be switched.

44. The apparatus of claim 42, wherein the plurality of leads and the secondary lead are electrically connected to a power source such that the polarity of the plurality of leads can be changed independently of the polarity of the secondary lead.

45. The apparatus of claim 42, wherein the plurality of leads and the secondary lead are electrically connected to a power source, wherein the polarity of the plurality of leads can be switched to have either the same polarity or to have opposing polarities for adjacent distal ends of the leads, and the polarity of the secondary lead can be switched between having a polarity and being neutral.

46. The apparatus of claim 42, wherein the distal secondary end includes a generally spherical shape having a cross-sectional dimension approximately equal to the dimension of the opening at the working end of the catheter.

47. The apparatus of claim 42, wherein the distal ends of the leads are configured to form a shape having a cross-sectional dimension no greater than the dimension of the distal secondary end when the distal ends are moved toward the longitudinal axis defined by the sheath.

48. The apparatus of claim 42, wherein the distal ends of the leads are configured to form, in combination with the secondary lead, a shape having a cross-sectional dimension no greater than the dimension of the distal secondary end when the distal ends are moved toward the longitudinal axis defined by the sheath.

49. The apparatus of claim 42, wherein the secondary lead includes a secondary lumen and a secondary opening formed in the distal secondary end such that the secondary opening is in fluid communication with the secondary lumen.

50. The apparatus of claim 49, wherein secondary lumen is configured to accept a guide wire.

51. The apparatus of claim 42, wherein the distal end of the leads each include a rounded convex surface which is uninsulated.

52. The apparatus of claim 37, wherein a temperature sensor is located on at least one of the distal ends of the plurality of leads.

53. The apparatus of claim 37, wherein the distal ends of the leads are arranged to occupy a plane perpendicular to the longitudinal axis defined by the sheath.

54. The apparatus of claim 37, wherein the distal ends of the leads are configured to form a generally spherical shape when the distal ends are moved toward the longitudinal axis defined by the sheath.

55. The apparatus of claim 37, wherein the working end of the catheter includes a tip having a soft durometer, the opening being formed in the tip.

56. The apparatus of claim 37, wherein the leads are electrically connected to a power source such that the polarity of each lead can be switched.

57. The apparatus of claim 56, wherein the leads are electrically connected to a power source such that the polarity of each lead is the same.

58. The apparatus of claim 56, wherein the leads are electrically connected to a power source such that the polarity of a first lead of said plurality of leads is opposite to the leads with distal ends adjacent to the distal end of the first lead.

59. The apparatus of claim 37, wherein a ring is attached to the inner member, and at least one lead of the plurality of leads is connected to the ring.

60. The apparatus of claim 59, wherein the ring is conductive and electrically connected to a power source so that the distal end of the one lead can deliver energy to ligate the anatomical structure.

61. The apparatus of claim 37 wherein the catheter comprises a lumen having an opening at the working end and is configured to conduct fluid such as drugs, dielectric fluid, heparin, or saline, through the catheter.

62. The apparatus of claim 61 wherein the lumen is centrally located in the catheter and is also adapted to receive a guide wire.

63. The apparatus of claim 61 wherein the lumen is located between an inner and outer sheath in the catheter.

64. The apparatus of claim 37 wherein the leads are mounted at the working end in a cantilever arrangement.

65. The apparatus of claim 37 wherein each lead includes a bend selected such that each lead tends to move outward away from the other leads.

66. The apparatus claim 65 wherein each lead includes a bend formed with an angle less than ninety degrees.

67. The apparatus of claim 37 wherein each lead comprises a rectangular cross section mounted in relation to the catheter such that the thinner dimension of the rectangular cross section is aligned with the direction that the distal end of the lead moves away from the axis.

68. An apparatus for applying energy from a power source to a hollow anatomical structure from within the hollow anatomical structure, the hollow anatomical structure having an inner wall, the power source being responsive to temperature signals to control the level of power, the apparatus comprising:

a catheter having a working end and a lumen configured for fluid delivery;

a plurality of expandable leads disposed at the working end in a cantilever mounting, wherein the leads are formed with a rectangular cross-section and are mounted to the catheter with a bend such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it, the leads also having a rounded, convex-shaped distal portion with an uninsulated distal tip, each lead electrically connected to the power source; and a temperature sensor located at a lead, the sensor providing temperature signals representative of the temperature sensed at the lead;

wherein the expandable leads are configured so as to maintain non-penetrating apposition with the inner wall to permit the catheter to be moved in the hollow anatomical structure at the same time that the leads are applying energy to the hollow anatomical structure.

69. The apparatus of claim 68 further comprising a secondary lead having a distal end and a length such that the distal end of the secondary lead extends past the distal end of the expandable leads.

70. An apparatus for applying energy from a power source to a vein from within the vein, the vein having an inner wall, the apparatus comprising:

a catheter having a working end;

a plurality of leads disposed at the working end, each lead having a distal portion at which energy may be applied to the inner wall of the vein, each lead connected to the power source;

a lead control device adapted to control the outward expansion of the leads from a contracted configuration to an expanded configuration at which the distal portions of the leads are in non-penetrating apposition with the inner wall of the vein;

wherein the leads are formed and mounted to the catheter such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it.

71. The apparatus of claim 70 wherein the leads are disposed in relation to the working end such that when expanded into non-penetrating apposition with the inner wall of the vein, the distal portions of the leads form a substantially symmetric arrangement of substantially evenly spaced distal ends.

72. The apparatus of claim 70 wherein the leads are disposed in relation to the working end such that when the leads are expanded into non-penetrating apposition with the inner wall of the vein, the distance between two mutually opposed distal ends is greater than the diameter of the working end.

73. The apparatus of claim 70 wherein the leads are mounted at the working end in a cantilever arrangement.

74. The apparatus of claim 70 wherein each lead includes a bend selected such that each lead tends to move outward away from the other leads.

75. The apparatus of claim 70 wherein each lead comprises a rectangular cross section mounted in relation to the catheter such that the thinner dimension of the rectangular cross section is aligned with the direction of expansion of the lead.

76. The apparatus of claim 70 wherein the catheter includes a guide wire lumen for receiving a guide wire and through which flushing fluid may be conducted to the working end of the catheter.

77. The apparatus of claim 70 further comprising a temperature sensor located at a lead, the sensor providing temperature signals representative of the temperature at the lead.

78. An apparatus for applying energy from a power source to a vein from within the vein, the vein having an inner wall, the apparatus comprising:
   a catheter having a working end;
   a plurality of leads disposed at the working end, each lead having a distal end configured to apply energy to the inner wall of the vein and each lead having a proximal end, each lead connected to the power source and each lead mounted at the proximal end to the working end in a cantilever arrangement;
   a lead control device adapted to control the outward expansion of the leads from a contracted configuration to an expanded configuration at which the distal ends of the leads are in non-penetrating apposition with the inner wall of the vein;
   wherein each lead comprises a bend formed in the lead, the bend selected to result in the leads expanding outwardly moving away from each other into non-penetrating apposition with the inner wall;
   wherein the leads are formed and mounted to the catheter such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it.

79. The apparatus of claim 78 wherein each lead comprises an electrode mounted at its distal end, the electrode having a rounded convex shape.

80. The apparatus of claim 78 wherein each lead comprises a rectangular cross section mounted in relation to the catheter such that the thinner dimension of the rectangular cross section is aligned with the direction of expansion of the lead.

81. An apparatus for applying energy from a power source to a hollow anatomical structure from within the hollow anatomical structure, the power source being responsive to temperature signals to control the level of power, the hollow anatomical structure having an inner wall, the apparatus comprising:
   a catheter having a working end and a lumen configured for fluid delivery, and a longitudinal axis;
   a plurality of expandable leads disposed at the working end, wherein the leads are formed and mounted to the catheter such that when in an unconfined configuration, the leads have sufficient strength to move themselves outward into non-penetrating apposition with the inner wall, and further, the leads are formed and mounted to the catheter such that they do not have sufficient strength to prevent the reduction of the diameter of the inner wall wherein as the inner wall reduces, the leads remain in non-penetrating apposition with the inner wall and move inward with it, the leads also having a distal portion with an uninsulated distal tip, each lead electrically connected to the power source, and the plurality of leads being axially staggered such that when expanded, one lead is located farther from the working end of the catheter than another lead; and
   a temperature sensor located at a lead, the sensor providing temperature signals representative of the temperature sensed at the lead;
   wherein the expandable leads are configured so as to permit the catheter to be moved in the hollow anatomical structure at the same time that the leads are in non-penetrating apposition with the inner wall and are applying energy to the hollow anatomical structure.

* * * * *

UNITED STATES PATENT AND TRADEMARK OFFICE
CERTIFICATE OF CORRECTION

PATENT NO. : 6,200,312 B1
DATED : March 13, 2001
INVENTOR(S) : Arthur W. Zikorus, et al.

It is certified that error appears in the above-identified patent and that said Letters Patent is hereby corrected as shown below:

Title page,
Under "U.S. PATENT DOCUMENTS", add the following"
-- 5,282,845   2/1994    Bush, et al.
   5,472,441   12/1995   Edwards, et al.
   5,709,224   1/1998    Behl, et al.
   5,827,268   10/1998   Laufer
   5,863,290   1/1999    Gough, et al. --.

Under "FOREIGN PATENT DOCUMENTS, add the following:
-- EP 0 629 382 A1   12/1994   EPO
   EP 0 738 501 A1   10/1996   EPO
   WO 93/21846       11/1993   PCT
   WO 94/21170       9/1994    PCT
   WO 95/10236       4/1995    PCT
   WO 96/32885       10/1996   PCT
   WO 97/06739       2/1997    PCT
   WO 97/17892       5/1997    PCT --.

Under "OTHER PUBLICATIONS, add the following:
-- Watts, G.T., Endovascular Diathermy Destruction of Internal Saphenous, British Medical Journal, October 7, 1992, p. 53.
O'Reilly, Kevin, Endovenus Diathermy Sclerosis of Varicose Veins, The Australian, New Zealand and Journal of Surgery, Vol. 47, No. 3, June 1977, pp. 393-395.
O'Reilly, Kevin, A Technique of Diathermy Sclerosis of Varicose Veins, The Australian, New Zealand Journal of Surgery Vol. 51, No. 4, August 1981, pp. 393-395.
Cragg, et al., Endovascular Diathermic Vessel Occlusion, Diagnostic Radiology, 144: pp. 303-308, July 1982.
Gradman, Venoscopic Obliteraton of Variceal Tributaries Using Monopolar Electrocautery, Journal of Dermatology Surgery Oncology, 1994, 20, pp. 482-485.
Inturri, Pathophysiology of Portal Hypertension, Journal of Vascular technology 19, (5-6): pp. 271-276, Dec. 1995 --.

UNITED STATES PATENT AND TRADEMARK OFFICE
CERTIFICATE OF CORRECTION

| | |
|---|---|
| PATENT NO. | : 6,200,312 B1 |
| DATED | : March 13, 2001 |
| INVENTOR(S) | : Arthur W. Zikorus, et al. |

It is certified that error appears in the above-identified patent and that said Letters Patent is hereby corrected as shown below:

Claims,
Column 19,
Lines 14 & 15, delete "an", and add therein -- a distal -- before "orifice".
Lines 18 & 19, delete ", each lead electrically connected to the power source".
Line 22, after "the", add -- distal end of the --.
Line 61, change "end", to read -- ends -- (2nd occur.) and before "leads", add -- plurality of --.

Column 21,
Lines 4 & 5 delete "an", and add therein -- a distal -- before "orifice".
Line 14, after "the", second occurrence, add -- distal end of the -- and replace "moving", with -- and move --.

Column 22, claim 41,
Change "46", to read -- 37 --.

Signed and Sealed this

Ninth Day of October 2001

*Attest:*

*Attesting Officer*

NICHOLAS P. GODICI
*Acting Director of the United States Patent and Trademark Office*